(12) United States Patent
Wang et al.

(10) Patent No.: US 8,951,473 B2
(45) Date of Patent: Feb. 10, 2015

(54) DEVICES AND METHODS FOR DETERMINATION OF SPECIES INCLUDING CHEMICAL WARFARE AGENTS

(75) Inventors: Fei Wang, Cambridge, MA (US);
Timothy M. Swager, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/920,612

(22) PCT Filed: Mar. 4, 2009

(86) PCT No.: PCT/US2009/001396
§ 371 (c)(1),
(2), (4) Date: Dec. 23, 2010

(87) PCT Pub. No.: WO2009/136978
PCT Pub. Date: Nov. 12, 2009

(65) Prior Publication Data
US 2011/0089051 A1    Apr. 21, 2011

Related U.S. Application Data

(60) Provisional application No. 61/033,593, filed on Mar. 4, 2008.

(51) Int. Cl.
*G01N 15/06* (2006.01)
*G01N 33/00* (2006.01)
(Continued)

(52) U.S. Cl.
CPC ............... *G01N 27/414* (2013.01); *B82Y 15/00* (2013.01); *B82Y 30/00* (2013.01); *B82Y 40/00* (2013.01);
(Continued)

(58) Field of Classification Search
USPC ............ 422/68.1, 82.01, 82.02; 977/953, 957
See application file for complete search history.

(56) References Cited

U.S. PATENT DOCUMENTS 3,450,878 A    6/1969   Pezdirtz et al.
3,915,706 A    10/1975  Limburg et al.
(Continued)

FOREIGN PATENT DOCUMENTS

CN    1995143 A    7/2007
JP    63-221278 A  9/1988
(Continued)

OTHER PUBLICATIONS

International Search Report and Written Opinion for PCT/US2008/003180 mailed Jun. 19, 2009.
(Continued)

*Primary Examiner* — Brian J Sines
(74) *Attorney, Agent, or Firm* — Wolf, Greenfield & Sacks, P.C.

(57) ABSTRACT

The application generally describes devices, systems, and methods for determination of one or more analytes. Embodiments described herein may be useful as sensors for analytes such as explosives, chemical warfare agents, and/or toxins. In some cases, chemiresistor or chemFET sensor devices for monitoring volatile organics, especially chemical warfare agents such as sarin, are described. Some embodiments comprise functionalized carbon nanotube/conjugated polymer composites (6) as sensing material. In some embodiments, the polymer is poly(3-hexylthiophene), 3PHT, optionally substituted with calixarenes, or hexafluoroisopropanol susbstituted polythiophene, HFIP-PT. Biosensing embodiments are also described, as well as methods of manufacturing the devices.

35 Claims, 36 Drawing Sheets

(51) Int. Cl.
*G01N 33/48* (2006.01)
*G01N 27/414* (2006.01)
*B82Y 15/00* (2011.01)
*B82Y 30/00* (2011.01)
*B82Y 40/00* (2011.01)
*C01B 31/02* (2006.01)

(52) U.S. Cl.
CPC ......... *C01B 31/0273* (2013.01); *C01B 2202/02* (2013.01); *C08G 2261/146* (2013.01); *C08G 2261/148* (2013.01); *C08G 2261/3223* (2013.01); *C08G 2261/94* (2013.01); *Y10S 977/953* (2013.01); *Y10S 977/957* (2013.01)
USPC ................. 422/82.02; 422/68.1; 422/82.01; 977/953; 977/957

(56) References Cited

U.S. PATENT DOCUMENTS

| | | | |
|---|---|---|---|
| 4,616,237 | A | 10/1986 | Pettigrew et al. |
| 5,753,088 | A | 5/1998 | Olk |
| 6,616,497 | B1 | 9/2003 | Choi et al. |
| 6,652,958 | B2 | 11/2003 | Tobita |
| 6,705,910 | B2 | 3/2004 | Sheu et al. |
| 6,902,658 | B2 | 6/2005 | Talin et al. |
| 7,014,743 | B2 | 3/2006 | Zhou et al. |
| 7,187,115 | B2 | 3/2007 | Seon |
| 7,303,875 | B1 | 12/2007 | Bock et al. |
| 7,365,100 | B2 | 4/2008 | Kuper et al. |
| 7,556,775 | B2 * | 7/2009 | McGill et al. ............. 422/88 |
| 7,854,826 | B2 * | 12/2010 | So et al. ............. 204/403.01 |
| 7,871,533 | B1 | 1/2011 | Haiping et al. |
| 8,187,887 | B2 | 5/2012 | Swager et al. |
| 8,212,132 | B2 | 7/2012 | Swager et al. |
| 8,426,208 | B2 | 4/2013 | Swager et al. |
| 8,456,073 | B2 | 6/2013 | Swager et al. |
| 8,735,313 | B2 | 5/2014 | Swager et al. |
| 2002/0037457 | A1 | 3/2002 | Choi |
| 2004/0161360 | A1 | 8/2004 | Ogawa et al. |
| 2006/0057927 | A1 | 3/2006 | Kang et al. |
| 2006/0063464 | A1 | 3/2006 | Kang et al. |
| 2006/0151382 | A1 | 7/2006 | Petrik |
| 2006/0174385 | A1 * | 8/2006 | Gruber et al. ............. 977/874 |
| 2006/0202168 | A1 | 9/2006 | Barrera et al. |
| 2007/0178477 | A1 | 8/2007 | Joiner et al. |
| 2007/0179272 | A1 * | 8/2007 | Tobe et al. ............. 528/397 |
| 2007/0295347 | A1 | 12/2007 | Paine et al. |
| 2008/0076816 | A1 | 3/2008 | Bianco et al. |
| 2008/0131658 | A1 | 6/2008 | Wakharkar et al. |
| 2008/0221240 | A1 | 9/2008 | Swager et al. |
| 2009/0058258 | A1 | 3/2009 | Chang et al. |
| 2009/0305089 | A1 * | 12/2009 | Minteer et al. ............. 429/13 |
| 2009/0306427 | A1 | 12/2009 | Martinez-Rubi |
| 2010/0028559 | A1 | 2/2010 | Yan et al. |
| 2010/0179054 | A1 | 7/2010 | Swager et al. |
| 2010/0222432 | A1 | 9/2010 | Hua |
| 2011/0081724 | A1 | 4/2011 | Swager et al. |
| 2011/0136007 | A1 | 6/2011 | Zhamu et al. |
| 2011/0171629 | A1 | 7/2011 | Swager et al. |
| 2012/0116094 | A1 | 5/2012 | Swager et al. |
| 2012/0171093 | A1 | 7/2012 | Swager et al. |
| 2012/0295360 | A1 | 11/2012 | Swager et al. |
| 2013/0113359 | A1 | 5/2013 | Swager et al. |
| 2014/0107326 | A1 | 4/2014 | Swager et al. |

FOREIGN PATENT DOCUMENTS

| | | |
|---|---|---|
| JP | 2008-047855 A | 2/2008 |
| WO | WO 01/10779 A1 | 2/2001 |
| WO | WO 2004/113275 A2 | 12/2004 |
| WO | WO 2006/104046 A1 | 10/2006 |
| WO | WO 2006/115486 A1 | 11/2006 |
| WO | WO 2007/033189 A1 | 3/2007 |
| WO | WO 2007/098578 A1 | 9/2007 |
| WO | WO 2007/143028 A2 | 12/2007 |
| WO | WO 2008/133779 A2 | 11/2008 |
| WO | WO 2009/085015 A1 | 7/2009 |
| WO | WO 2009/136978 A2 | 11/2009 |
| WO | WO 2010/022164 A1 | 2/2010 |

OTHER PUBLICATIONS

International Preliminary Report on Patentability for PCT/US2008/003180 mailed Sep. 17, 2009.
Invitation to Pay Additional Fees for PCT/US2009/001396 mailed Dec. 10, 2009.
International Search Report and Written Opinion for PCT/US2009/001396 mailed Apr. 22, 2010.
International Preliminary Report on Patentability for PCT/US2009/001396 mailed Sep. 16, 2010.
International Search Report and Written Opinion for PCT/US2009/006512 mailed Oct. 22, 2010.
International Preliminary Report on Patentability for PCT/US2009/006512 mailed Jun. 23, 2011.
Invitation to Pay Additional Fees for PCT/US2010/051610 mailed Dec. 27, 2011.
Invitation to Pay Additional Fees for PCT/US2010/055395 mailed Dec. 7, 2011.
[No Author Listed] TGP-H Carbon Fiber Paper. Toray Automotive Solutions. Toray Industries (America), Inc. Available at http://www.toray-auto.us/poductrs/carbon_papers_fuel$_1$_cells.html. Last accessed Nov. 19, 2010. 2 pages.
Albert et al., Cross-reactive chemical sensor arrays. Chem Rev. Jul. 12, 2000;100(7):2595-626.
Bai et al., Gas Sensors Based on Conducting Polymers. Sensors. 2007;7:267-307.
Baughman et al., Carbon Nanotubes—The Route Toward Applications. Science. 2002;297(2):787-92.
Becker et al., The Influence of Surface Strain on the Chemical Reactivity of Fullerene Ions: Addition Reactions with Cyclopentadiene and 1,3-cycolhexadiene. International Journal of Mass Spectrometry and Ion Processes. 1997;167/168:519-24.
Chen et al., Dissolution of Full-Length Single-Walled Carbon Nanotubes. J Phys Chem B. 2001;105:2525-28.
Chen et al., Noncovalent functionalization of carbon nanotubes for highly specific electronic biosensors. Proc Natl Acad Sci U S A. Apr. 29, 2003;100(9):4984-9. Epub Apr. 15, 2003.
Coffey et al., Conducting Polymer/Graphite Fiber Composites for High Charge Density Battery Electrodes. Lithium batteries—Symposium. Proceedings—Electrochemical Society. New Orleans, LA. Oct. 1993. The Society. 1994;94-4:258-68.
Coffey et al., High charge density conducting polymer/graphite fiber composite electrodes for battery applications. J Electrochem Soc. 1995;142(2):321-25.
Collins et al., Extreme oxygen sensitivity of electronic properties of carbon nanotubes. Science. Mar. 10, 2000;287(5459):1801-4.
Diederich et al., Covalent Fulleren Chemistry. Science. 1996;271:317-23.
Dwyer et al., DNA-functionalized single-walled carbon nanotubes. Nanotechnology. 2002;13(5):601-04.
Giordani et al., Multifunctional hybrid materials composed of [60]fullerene-based functionalized-single-walled carbon nanotubes. Carbon. 2009;47(3):578-88.
Guo et al., Covalently bridging gaps in single-walled carbon nanotubes with conducting molecules. Science. Jan. 20, 2006;311(5759):356-9.
Hahm et al., Direct Ultrasensitive Electrical Detection of DNA and DNA Sequence Variations Using Nanowire Nanosensors. Nano Letters. 2004; 4(1):51-54.
Janata et al., Conducting polymers in electronic chemical sensors. Nat Mater. Jan. 2003;2(1):19-24.
Jung et al., Covalent attachment and hybridization of DNA oligonucleotides on patterned single-walled carbon nanotube films. Langmuir. Sep. 28, 2004;20(20):8886-91.
Kamat et al., Self-Assembled Linear Bundles of Single Wall Carbon Nanotubes and Their Alignment and Deposition as a Film in a dc Field. J Am Chem Soc. 2004;126(34):10757-62.

(56) References Cited

OTHER PUBLICATIONS

Khare et al., Carbon Nanotube Based Composites—A Review. Journal of Minerals & Materials Characterization & Engineering. 2005; 4(1):31-46.
Kolmakov et al., Chemical Sensing and Catalysis by One-Deminsional Metal-Oxide Nanostructures. Annu Rev Mater Res. 2004;34:151-80.
Kong et al., Nanotube molecular wires as chemical sensors. Science. Jan. 28, 2000;287(5453):622-5.
Liu et al., Fullerene pipes. Science. May 22, 1998;280(5367):1253-6.
Lobez et al., Radiation Detection: Resistivity Responses in Functional Poly (Olefin Sulfone)/Carbon Nanotube Composites. Angew Chem Int Ed. 2010; 49:95-98.
Lutz, 1,3-Dipolar cycloadditions of azides and alkynes: a universal ligation tool in polymer and materials science. Angew Chem Int Ed. 2007; 46:1018-25.
Maggini et al., Addition of Azomethine Ylides to $C_{60}$: Synthesis, Characterization, and Functionalization of Fullerene Pyrrolidines. J Am Chem Soc. 1993;115: 9798-99.
McQuade et al., Conjugated Polymer-Based Chemical Sensors. Chem Rev. 2000;100:2537-74.
Moses et al., The growing applications of click chemistry. Chem Soc Rev. Aug. 2007;36(8):1249-62. Epub May 3, 2007.
O'Donovan et al., Phosphine-catalysed cycloaddition of buta-2,3-dienoates and but-2-ynoates to [60]fullerene. Chem Commun. 1997:81-82.
Park et al., Enhancement of the field-effect mobility of poly(3-hexylthiophene)/functionalized carbon nanotube hybrid transistors. Org Electon. 2008;9:317-22.
Pederson et al., Core particle, fiber, and transcriptionally active chromatin structure. Annu Rev Cell Biol. 1986;2:117-47.
Potyrailo, Polymeric Sensoir Materials: Toward an Alliance of Combinatorial and Rational Design Tools? Agnew Chem Int Ed. 2006;45:702-23.
Prato et al., Fulleropyrrolidines: A Family of Full-Fledged Fullerene Derivatives. Acc Chem Res. 1998;31(9):519-26.
Preda et al., Addition of Dihalocarbenes to Corannulene. A Fullerene-Type Reaction. Tetrahedron Letters. 2000;41: 9633-37.
Qi et al., Toward Large Arrays of Multiplex Functionalized Carbon Nanotube Sensors for Highly Sensitive and Selective Molecular Detection. Nano Lett. 2003;3(3):347-51.
Rostovtsev et al., A stepwise huisgen cycloaddition process: copper(I)-catalyzed regioselective "ligation" of azides and terminal alkynes. Angew Chem Int Ed Engl. Jul. 15, 2002;41(14):2596-9.
Santhanam et al., A chemical sensor for chloromethanes using a nanocomposite of multiwalled carbon nanotubes with poly(3-methylthiophene). Sensors and Actuators B. 2005;106:766-71.
Scott, Fragments of Fullerenes: Novel Syntheses, Structures and Reactions. Pure & Appl Chem., 1996;68(2):291-300.
Serp et al., Carbon Nanotubes and Nanofibers in Catalysis. Applied Catalysis A: General. 2003;253:337-58.
Shu et al., Phosphine-catalysed [3+2] cycloadditions of buta-2,3-dienoates with [60]fullerene. Chem Commun. 1997;79-80.
Silverman, The Organic Chemistry of Drug Design and Drug Action. 2nd ed. 2004;29-32.
Snow et al., Chemical detection with a single-walled carbon nanotube capacitor. Science. Mar. 25, 2005;307(5717):1942-5.
Star et al., Electronic Detection of Specific Protein Binding Using Nanotube FET Devices. Nano Lett. 2003;3(4):459-63.
Star et al., Nanoelectronic Carbon Dioxide Sensors. Adv Mater. 2004;16(22):2049-52.
Sun et al., Functionalized Carbon Nanotubes: Properties and Applications. Acc Chem Res. 2002;35(12):1096-1104.
Swager, The Molecular Wire Approach to Sensory Signal Amplificiation. Acc Chem Res. 1998;31:201-07.
Tasis et al., Chemistry of Nanotubes. *Chem Rev.* 2006;106:1105-36.
Toal et al., Polymer sensors for niroaromatic explosives detection. Mater Chem. 2006;16:2871-83.
Tombler et al., Reversible electromechanical characteristics of carbon nanotubes under local-probe manipulation. Nature. 2000;405:769-72.
Wang et al., Carbon Nanotube/Polythiophene Chemiresistive Sensors for Chemical Warfare Agents. J Am Chem Soc. 2008;130:5392-93.
Wang et al., Novel multicomponent reaction of [60]fullerene: the first example of 1,4-dipolar cycloaddition reaction in fullerene chemistry. Org Biomol Chem. 2006;4:4063-64.
Wei et al., Covalent functionalization of single walled carbon nanotubes and fullerenes via a switterion approach. Chemical Abstracts. 2007. 2 pages.
Wei et al., Multifunctional chemical vapor sensors of aligned carbon nanotube and polymer composites. J Am Chem Soc. Feb. 8, 2006;128(5):1412-3.
Weizmann et al., DNA-CNT nanowire networks for DNA detection. J Am Chem Soc. Mar. 16, 2011;133(10):3238-41. Epub Feb. 22, 2011.
Zaharescu et al., Electrical properties of polyolefin blends under eradiation exposure. ICSD 2004. Proceedings of the 2004 Inter National Conference on Solid Dielectrics. Toulouse, France. Jul. 5-9, 2004. IEEE. Jul. 5, 2004;1:367-69.
Zhang et al., Covalent Functionalization of Singled Walled Carbon Nanotubes and Fullerenes via a Zwitterion Approach. Prep Pap.-Am Chem Soc, Div Fuel Chem.. 2007;52(1):126-28.
Zhang et al., Electochemically Functionalized Single-Walled Carbon Nanotube Gas Sensor. Electroanalysis. 2006;18(12):1153-58.
Zhang et al., Functionalization of single-walled carbon nanotubes and fullerenes via a dimethyl acetylenedicarboxylate-4-dimethylaminopyridine zwitterion approach. J Am Chem Soc. Jun. 27, 2007;129(25):7714-5. Epub Jun. 2, 2007.
Zhang et al., Modular Functionalization of Carbon Nanotubes and Fullerenes. J Am Chem Soc. 2009;131:8446-54.
Zhou et al., A New Method for the Functionalization of [60] Fullerene: An Unusual 1,3-Dipolar Cycloaddition Pathway Leading to a $C_{60}$ Housane Derivative. Organic Letters. 2005;7(26):5849-51.
International Search Report and Written Opinion for PCT/US2010/051610 mailed Mar. 5, 2012.
International Search Report and Written Opinion for PCT/US2010/055395 mailed Mar. 20, 2012.
Raval et al., Determining ionizing radiation using sensors based on organic semiconducting material. Appl Phys Lett. 2009;94:123304-1-123304-3.
Tang et al., Measurement of ionizing radiation using carbon nanotube field effect transistor. Phys Med Biol. Feb. 7, 2005;50(3):N23-31.
Yates et al., The absorption coefficient spectrum and radiatoin degradation of poly (butene-1 sulfone) in the soft X-ray region. J Poly Sci Part B Poly Phys. 1993;31:1837-44.
International Preliminary Report on Patentability for PCT/US2010/051610 mailed Apr. 19, 2012.
International Preliminary Report on Patentability for PCT/US2010/055395 mailed May 18, 2012.
Georgakilas et al., Organic functionalization of carbon nanotubes. J Am Chem Soc. Feb. 6, 2002;124(5):760-1.
Kubat et al., Degradation of pyrene by UV radiation. Journal of Photochemistry and Photobiology A: Chemistry. 2000;132:33-36.
International Preliminary Report on Patentability for PCT/US2011/059155 mailed Jul. 11, 2013.
International Preliminary Report on Patentability for PCT/US2011/059168 mailed Jul. 18, 2013.
International Search Report and Written Opinion for Application No. PCT/US2013/029621 mailed May 8, 2013.
Englert et al., Covalent bulk functionalization of graphene. Nature Chemistry. Apr. 2011;3:279-86.
Liang et al., $Co_3O_4$ nanocrystals on graphene as a synergistic catalyst for oxygen reduction reaction. Nat Mater. Oct. 2011;10(10):780-6.
Loh et al., The chemistry of graphene. Journal of Materials Chemistry. Mar. 28, 2010;20(12):2277-89.
Ramanathan et al., Functionalized graphene sheets for polymer nanocomposites. Nat Nanotechnol. Jun. 2008;3(6):327-31. Epub May 11, 2008.
Shih et al., Bi- and trilayer graphene solutions. Nature Nanotechnology. Jul. 2011;6:439-45.

(56) References Cited

OTHER PUBLICATIONS

Wang et al., High-yield synthesis of few-layer graphene flakes through electrochemical expansion of graphite in propylene carbonate electrolyte. J Am Chem Soc. Jun. 15, 2011;133(23):8888-91. Epub May 17, 2011.

Zhu et al., Covalent Functionalization of Surfactant-Wrapped Graphene Nanoribbons. Chemistry of Materials. 2009;21:5284-91.

International Search Report and Written Opinion for PCT/US2011/059155 mailed Jun. 25, 2013.

International Search Report and Written Opinion for PCT/US2011/059168 mailed Jun. 19, 2013.

Bekyarova et al., Chemical modification of epitaxial graphene: spontaneous grafting of aryl groups. J Am Chem Soc. Feb. 4, 2009;131(4):1336-7.

Haubner et al., The route to functional graphene oxide. Chemphyschem. Jul. 12, 2010;11(10):2131-9.

Paul et al., Sequestration and selective oxidation of carbon monoxide on graphene edges. Journal of Physics: Condensed Matter. Sep. 2, 2009;21(35):355008.

Wang et al., Synthesis of enhanced hydrophilic and hydrophobic graphene oxide nanosheets by a solvothermal method. Carbon. Jan. 1, 2009;47(1):68-72.

Y00 et al., Enhanced electrocatalytic activity of Pt subnanoclusters on graphene nanosheet surface. Nano Lett. Jun. 2009;9(6):2255-9.

Zhao et al., Synthesis and characterization of water soluble single-walled carbon nanotube graft copolymers. J Am Chem Soc. Jun. 8, 2005;127(22):8197-203.

[No Author] Definition of "ketone," accessed online at http://dictionary.reference.com/browse/ketone?s=t on Jun. 14, 2014.

* cited by examiner

66

P3HT a (a) Pd(PPh$_3$)$_4$, DMF, 80°C; (b) 1) n-BuLi, Hex/THF, -40°C; 2) HEXAFLUOROCETONE, 0°C; (c) Br$_2$, HOAc, 60°C.

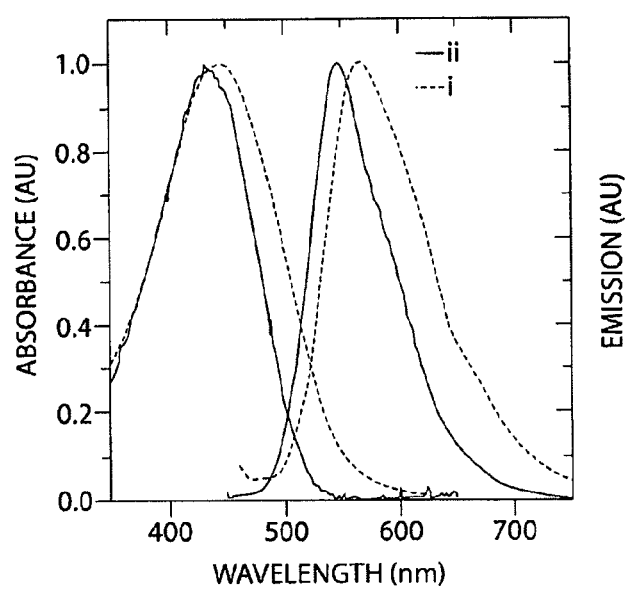
Fig. 18
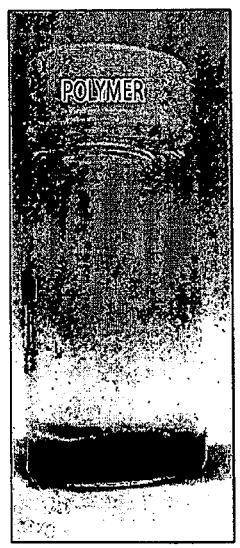 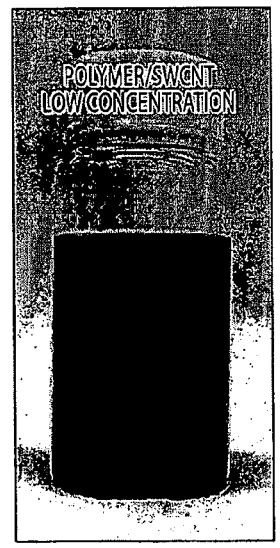 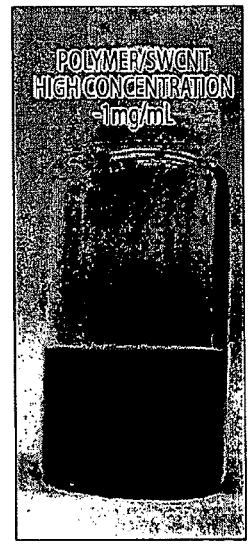
Fig. 19A    Fig. 19B    Fig. 19C

91

94

DEVICES AND METHODS FOR DETERMINATION OF SPECIES INCLUDING CHEMICAL WARFARE AGENTS

RELATED APPLICATIONS

This application claims priority under 35 U.S.C. §119(e) to U.S. Provisional Application Ser. No. 61/033,593, filed Mar. 4, 2008, the contents of which are incorporated herein by reference.

STATEMENT REGARDING FEDERALLY SPONSORED RESEARCH OR DEVELOPMENT

This invention was made with the support under the following government contract: DAAD19-02-D-0002, awarded by the Army Research Office. The government has certain rights in the invention.

FIELD OF THE INVENTION

The present invention generally relates to devices and systems for determining analytes, and related methods.

BACKGROUND OF THE INVENTION

New generations of low power, low cost, and portable sensing devices may be used in technologies related to homeland security, monitoring of agriculture, medical, and manufacturing environments, and other applications. For example, chemiresistors are chemical sensors based on a change in resistance in response to the binding of analytes and can be used for analyte detection, identification, and/or quantification. Chemiresistors generally have low power consumption and can give high precision resistance measurements. Typically, chemiresistors include a material capable of responding to a species (e.g., analyte). For example, several materials have been utilized as gas sensors, including metal oxides, organic semiconductors, and other materials. However, many of the current devices are limited by complex fabrication processes, high power consumption, and/or poor sensitivity. In some cases, organic materials have been considered as chemiresistor materials since molecular recognition elements may be readily integrated into their structures. However, such materials have been limited by electrostatic/dielectric interferences and fragile organic metal-interfaces.

Carbon-containing molecules such as graphite, carbon nanotubes, and fullerenes have attracted attention due to their unique mechanical and electronic properties, as well as their potential applications in nanotechnology. For example, carbon nanotube (CNT) field effect transistors have been studied as chemical and biological sensors. Their resistance can change drastically in the presence of analytes via, for example, charge transfer (e.g., doping), carrier pinning, and/or modification of the Schottky barrier at the carbon nanotube/metal contact. However, current applications have largely been limited by complexities associated with device fabrication.

Accordingly, improved devices and methods are needed.

SUMMARY OF THE INVENTION

The present invention relates to devices for determining an analyte, comprising a first electrode and a second electrode; a sensor material in electrochemical communication with the first and the second electrodes, wherein resistance to current flow between the first and second electrode is affected by the sensor material; wherein the sensor material comprises a plurality of carbon nanotubes and a polymer material integrally connected to at least a portion of the plurality of carbon nanotubes, such that the carbon nanotubes are substantially contained within the polymer material; and wherein the analyte, if present, interacts with the sensor material to affect resistance to current flow between the first and second electrodes, thereby generating a signal in the device by which the analyte is determined.

In some embodiments, the present invention provides methods for determining an analyte. The method may be performed using a device of the present invention. In some cases, a method for determining an analyte comprises providing a device comprising a first electrode, a second electrode, and a sensor material in electrical communication with the first and second electrodes, wherein the sensor material comprises carbon nanotubes; exposing the device to a sample suspected of containing an analyte wherein the analyte, if present, interacts with the sensor material to cause a change in resistance between the first and second electrodes; and determining the change in resistance between the first and second electrodes, thereby determining the analyte, wherein, when the analyte is present in an amount equal to or less than 1.0 ppm, the change in resistance comprises a change of at least 1%.

The present invention also provides methods for fabricating a device, comprising providing a mixture comprising a plurality of carbon nanotubes and a polymer material, or precursor thereof; processing the mixture to form a sensor material on the surface of a substrate, the sensor material comprising the carbon nanotubes associated with the polymer material, or precursor thereof; and forming at least one electrode material on the surface of the a substrate or in contact with the sensor material.

BRIEF DESCRIPTION OF THE DRAWINGS

FIG. 18 shows the UV-vis absorption and fluorescence emission spectra of an HFIP-PT polymer (i) in film, and (ii) in solution.

FIG. 19 shows a photograph of an HFIP-PT polymer solution comprising (A) no single-walled carbon nanotubes, (B) a low concentration of single-walled carbon nanotubes (e.g., less than 1 mg/mL), and (C) a high concentration of single-walled carbon nanotubes (e.g., about 1 mg/mL).

Figure 1A:
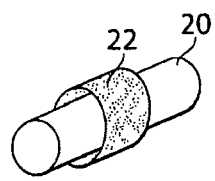
FIG. 1 shows (A-E) examples of carbon nanotubes that are substantially contained within a polymer material, according to some embodiments of the invention, and (F-G) carbon nanotubes that substantially contained within a polymer material.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally provides devices and systems capable of interacting with one or more species (e.g., analyte) to produce an observable signal from the device, and related methods. The signal may, in some cases, provide information relating to the presence, identity, amount, and/or other characteristic of the one or more species.

In some cases, the present invention provides methods for the determination of at least one analyte. The analyte may be determined by monitoring, for example, a change in a signal of a material (e.g., sensor material) present within the device, upon exposure to the analyte. In some cases, the change in signal may be associated with an interaction between the device and the analyte. The signal may comprise an electrical, optical, or other property of the device, as described further below. For example, the method may involve use of a component having a resistance, where the resistance of the component is affected by (e.g., responsive to) an analyte. Some embodiments of the invention may also provide devices, or systems comprising a plurality of devices, for determination of an analyte. In some embodiments, devices described herein may be useful as sensors for the vapor phase detection of analytes such as explosives, chemical warfare agents, and/or toxins. Some embodiments of the invention may be advantageous in that the high sensitivity and/or selectivity of the devices can allow for the reliable detection of analytes at low concentrations. For example, the analyte (e.g., DMMP) may be determined when present in only trace quantities.

An advantageous feature of the invention may provide the ability to readily incorporate (e.g., process) materials such as carbon nanotubes into devices. For example, devices of the invention may include materials (e.g., carbon nanotubes) which might otherwise be difficult to process using previous methods, for example, due to insolubility of the materials and/or complex synthetic procedures needed to fabricate the materials. Some embodiments of the invention provide simplified fabrication methods for devices comprising materials such as carbon nanotubes.

In some embodiments, methods for determining an analyte are provided. As used herein, the term "determining" generally refers to the analysis of a species or signal, for example, quantitatively or qualitatively (whether the analyte is present and/or in what amount or concentration), and/or the detection of the presence or absence of the species or signals. "Determining" may also refer to the analysis of an interaction between two or more species or signals, for example, quantitatively or qualitatively, and/or by detecting the presence or absence of the interaction. For example, the method may include the use of a device capable of producing a first, determinable signal (e.g., a reference signal), such as an electrical signal, an optical signal, or the like, in the absence of an analyte. The device may then be exposed to a sample suspected of containing an analyte, wherein the analyte, if present, may interact with one or more components of the device to cause a change in the signal produced by the device. Determination of the change in the signal may then determine the analyte.

In some embodiments, the change in signal may occur upon interaction between the analyte and at least a portion or component of the device. For example, the device may comprise a sensor material that interacts with an analyte to produce a change in signal. In some embodiments, the analyte may contact, or may be positioned in sufficient proximity to, the sensor material, or may permeate an interior portion of the sensor material. In some embodiments, a volumetric or dimensional change (e.g., increase, decrease) of the sensor material may occur upon interaction with an analyte. For example, the sensor material may "swell" upon absorption of the analyte, wherein the change in volume may produce a change in a property of the sensor material. In some cases, the interaction between the sensor material and the analyte may comprise a reaction, such as a charge transfer reaction.

In some embodiments, the sensor material may comprise a conductive species, such that interaction between the sensor material and an analyte produces a change in an electrical property of the device. For example, the sensor material may comprise a conductive species (e.g., carbon nanotube) associated with (e.g., integrally connected to and/or supported by) a polymer material, as described more fully below. The sensor material may be arranged in electrical communication with two electrodes and may have a particular current, voltage, and/or resistance (e.g., signal). Upon interaction with an analyte, the current, voltage, and/or resistance of the sensor material may be affected (e.g., may increase or decrease) such that a change in signal is produced. In some cases, the change in signal may be associated with a charge transfer reaction and/or binding interaction between the conductive species and the analyte. In some cases, the change in the signal may be associated with a change in the orientation and/or arrangement of the conductive species, for example, upon swelling of the sensor material. Without wishing to be bound by theory, the change in signal may, in some cases, be attributed to a disruption in the conductive pathways between the conductive species (e.g., carbon nanotubes) upon swelling of the sensor material.

Upon determination of the analyte, the method may further comprise treating the sensor material to substantially remove the analyte such that the original or reference signal (e.g., the signal produced prior to exposure to the analyte) may be reproduced. That is, the sensor material may be "refreshed" or regenerated for subsequent use. In an illustrative embodiment, a device may undergo a change in electrical resistance upon exposure to an analyte. The device may then be treated (e.g., heated) such that the analyte degasses from the device and the resistance of the current flow may return to a baseline resistance. In some embodiments, the sensor material may comprise carbon nanotubes, wherein removal of the analyte from the sensor material may re-establish conductive pathways between the carbon nanotubes.

Methods of the invention may advantageously determine an analyte at relatively low concentrations of analyte. In some embodiments, the analyte may be present in an amount equal to or less than about 1.0 ppm, less than about 0.6 ppm, less than about 10 ppb, or, in some cases, less than about 5 ppb. In some cases, the device may exhibit high sensitivity in that a determinable change in signal may be observed in the presence of low concentrations of analyte. For example, the device may undergo a change in resistance upon exposure to an analyte. The change in resistance may be at least about 1%, at least about 2%, at least about 3% at least about 5% at least about 10%, at least about 50%, at least about 100%, or at least about 200%. In some cases, the analyte is present in an amount equal to or less than about 1.0 ppm and the change in resistance comprises a change of at least about 1%. In some cases, the analyte is present in an amount equal to or less than about 0.1 ppm and the change in resistance comprises a change of at least about 1%.

In some cases, methods described herein may determine an analyte with relatively high selectivity and/or specificity. For example, the device may comprise a sensor material that is responsive to a particular analyte and is substantially unresponsive to other species or is responsive to a lesser degree, such that the change in signal may be attributed to an interaction between the sensor material and the particular analyte. In some cases, the method may involve determination of more than one analyte (e.g., at least two or more types of analytes) present within a sample. For example, the interaction between a first analyte and a sensor material may give a first change in an electrical properties of the sensor material, while the interaction between a second analyte and the sensor material may give a second, different change in an electrical properties of the sensor material, such that distinguishable changes in signal may be determined for both the first analyte and the second analyte.

Some embodiments of the invention provide devices for determining an analyte. As described herein, the device may comprise a sensor material that is responsive to one or more analytes. The sensor material may comprise a material that is capable of undergoing a change in one or more properties upon exposure to an analyte. For example, the sensor material may include a conductive material having electrical properties that may be affected by the presence of an analyte. In some cases, the sensor material may include a luminescent material having optical properties that may be affected by the presence of an analyte. In some embodiments, the sensor material may include a material capable of undergoing a volumetric or dimensional change upon exposure to an analyte. The sensor material may also comprise one or more binding sites that interact with an analyte.

The sensor material may, in some cases, comprise a conductive species and may be arranged in electrochemical communication with one or more electrodes. The conductive species may include inorganic materials (e.g., metals, alloys, semiconductors), organic materials (e.g., polymer materials), organometallic materials, and/or combinations thereof. For example, the sensor material may include carbon nanotubes, including single-walled carbon nanotubes and/or multi-walled carbon nanotubes. In some embodiments, the carbon nanotubes may be associated with a polymer material integrally connected to at least a portion of the plurality of carbon nanotubes. The term "integrally connected," when referring to two or more objects, means objects that do not become separated from each other during the course of normal use, i.e., separation of the objects generally requires at least the use of tools, and/or by causing damage to at least one of the components, for example, by breaking, peeling, dissolving, etc.

For example, the sensor material may comprise carbon nanotubes and a polymer material, such that the carbon nanotubes are substantially contained within the polymer material. As used herein, a species that is "substantially contained within a polymer material" refers to a species associated with a polymer material that essentially completely circumscribes or surrounds at least a portion of the species. For example, carbon nanotubes substantially contained within a polymer material, when viewed along the long axis of a carbon nanotube, may have a layer of polymeric material that essentially completely surrounds the carbon nanotube, or portion thereof. In some cases, the carbon nanotube may not necessarily be surrounded in three dimensions along a cross-section of the carbon nanotube, but a portion of the carbon nanotube may be at least enclosed by the polymeric material when viewed along the long axis of the carbon nanotube. In some cases, the polymer material may essentially completely circumscribe at least a portion of the carbon nanotube. In some cases, the polymer material is a polymer matrix within which the carbon nanotubes are dispersed (e.g., a polymer support material). In some cases, the carbon nanotube may have some portions that are substantially free of polymer material, but at least a portion of the carbon nanotube is essentially completely circumscribed by the polymer material. For example, a carbon nanotube may have an exposed portion that contacts an underlying substrate, but a portion of the carbon nanotube may be substantially contained within a polymer material.

Figure 1B:
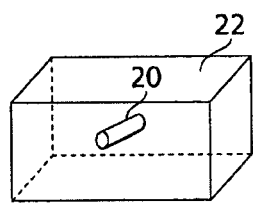
Figure 1C:
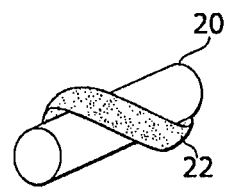
Figure 1D:
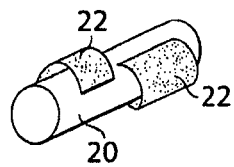
Figure 1E:
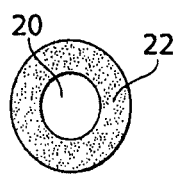

FIGS. 1A-1E show examples of a carbon nanotube 20 that is substantially contained within a polymer material. For example, FIG. 1A shows carbon nanotube 20 essentially completely circumscribed by polymer material 22 at a cross-section of the carbon nanotube, while FIG. 1B shows carbon nanotube 20 that is essentially completely contained within polymer material 22. As shown in FIG. 1C, carbon nanotube 20 is substantially contained within polymer material 22 in that various portions of carbon nanotube 20 are coated with polymer material 22, resulting in carbon nanotube 20 being essentially completely circumscribed by polymer material 22, when viewed along the long axis of carbon nanotube 20. Similarly, FIG. 1D shows carbon nanotube 20 which has been partially coated by polymer material 22 on one portion of carbon nanotube 20 and partially coated by polymer material 22 on another portion of carbon nanotube, such that, when viewed along the long axis of carbon nanotube, carbon nanotube 20 is substantially contained within polymer material 22. To further illustrate, FIG. 1E shows the carbon nanotube in FIGS. 1A-1D as viewed along the long axis of the carbon nanotubes, wherein carbon nanotube 20 is essentially completely circumscribed by polymer material 22.

Figure 1F:
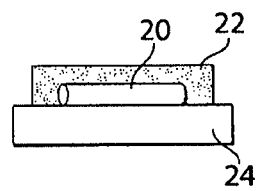
Figure 1G:
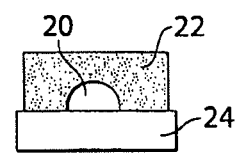

By contrast, a carbon nanotube having a substantial portion of its surface directly, integrally connected to an underlying substrate, such that a polymer material contacting the carbon nanotube does not circumscribe at least a portion of the carbon nanotube, may not be substantially contained within the polymer material. For example, a carbon nanotube synthesized or grown on the surface of a substrate, such that a substantial portion along the long axis of the carbon nanotube directly contacts the substrate, is not substantially contained within a polymer material, as described herein. For example, FIGS. 1F-1G show carbon nanotubes that may be in contact with a polymer material but are not substantially contained within polymer material. As shown in FIG. 1F, a carbon nanotube 20 that has been formed or grown on substrate 24 may not be essentially completely circumscribed by polymer material 22. FIG. 1G shows that the carbon nanotube of FIG. 1F, when viewed along the long axis of carbon nanotube, may not be essentially completely circumscribed by polymer material 22.

In some cases, the polymer material may comprise a conjugated polymer. The conjugated polymer may, in some embodiments, be used alone or in combination with a conductive species to facilitate the transport of charged species within the device. For example, the polymer material may comprise a polyarylate, such as polythiophene or poly(3-hexylthiophene), or copolymers thereof. In some embodiments, the polymer material includes a group comprising an acidic proton, such as fluorinated alcohol. In some cases, the polymer material comprises a hexafluoroisopropanol substituted polythiophene. In an illustrative embodiment, a device of the present invention may comprise a sensor material comprising a conductive species and a polymer material (e.g., a conjugated polymer), a first electrode, and a second electrode, wherein the sensor material may be arranged to be in electrochemical communication with the first and second electrodes. Upon exposure to an analyte, a change in an electrical property of the conjugated polymer may be affected by the interaction of the analyte with the sensor material.

In some embodiments, the sensor material may comprise one or more binding sites to facilitate interaction between the analyte and the sensor material. The binding site may be positioned within the sensor material such that interaction of the analyte with the binding site causes a determinable change in signal upon exposure to an analyte. For example, a sensor material may comprise a binding site positioned in sufficient proximity physically, or within sufficient electronic or inductive communication range, to one or more components of the device able to generate a signal. The binding site may be covalently attached to a component (e.g., sensor material) of the device, or may be dispersed within a component of the device. In some embodiments, the sensor material may comprise a plurality of binding sites.

The binding site may be selected to enhance the sensitivity of the interaction between the analyte and the sensor material. For example, incorporation of a plurality of binding sites within the device may improve the interaction between the sensor material and the analyte, producing a large change in signal. In some cases, the binding site may strongly bind the analyte, allowing the sensor material and the analyte to interact for a sufficient period of time such that a determinable signal may be observed. The binding site may be also selected to enhance the selectivity of the interaction between the analyte and the sensor material. For example, binding sites may be selected such that the sensor material interacts with a particular analyte to a greater extent than with other species present in a sample. That is, the sensor material may distinguish between different species present within a sample. In some cases, the sensor material and a particular analyte may interact for a sufficient period of time, wherein the sensor material and other species present in the sample interact for a relatively smaller period of time, or not at all. In some embodiments, incorporation of a binding site within the sensor material may increase the binding efficiency of the analyte by at least about 5%, at least about 10%, at least about 20%, at least about 40%, at least about 60%, at least about 80%, at least about 100%, at least about 200%, or greater.

Figure 2A:
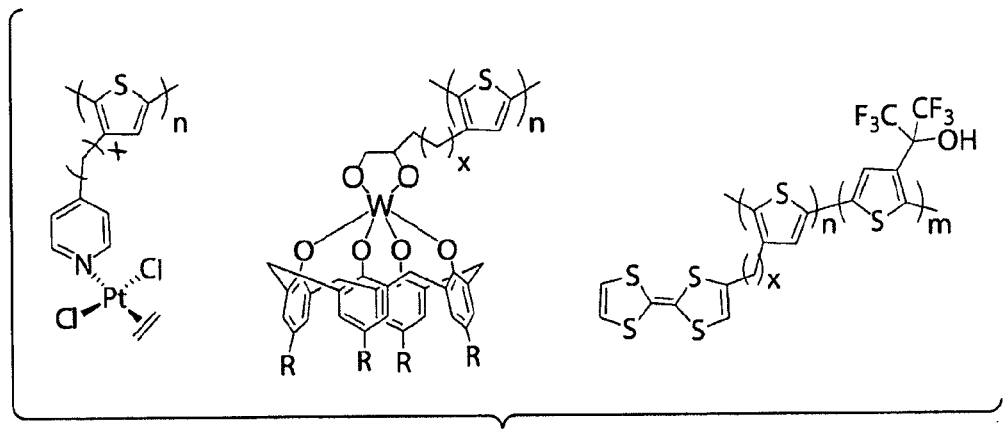
FIG. 2A shows examples of polymer materials (e.g. P3HT) covalently bound to a binding site, according to some embodiments of the invention.
Figure 2B:
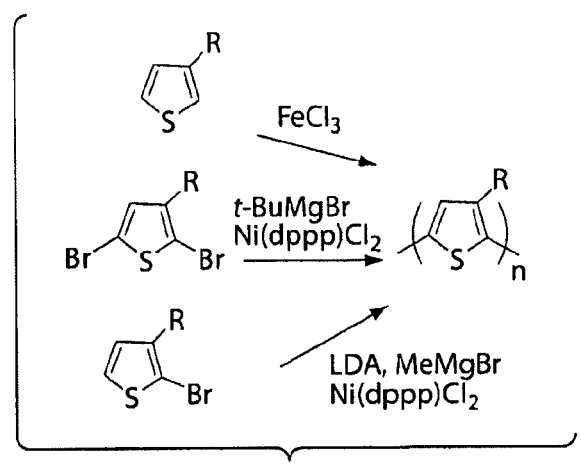
FIG. 2B shows the synthesis of substituted polythiophenes, according to some embodiments of the invention.
Figure 2C:
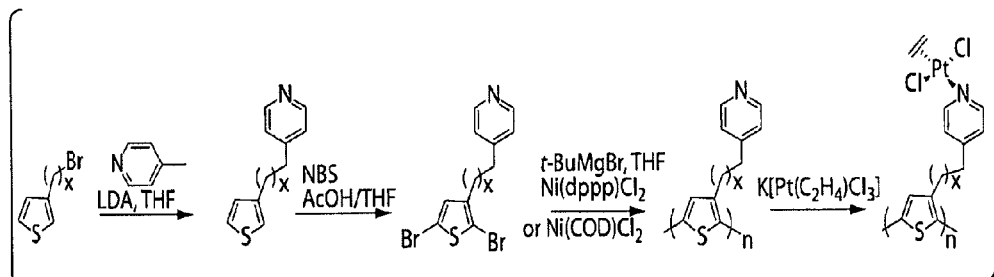
FIGS. 2C-2E shows examples the synthesis of polythiophenes covalently bound to binding sites, according to some embodiments of the invention.
Figure 2D:
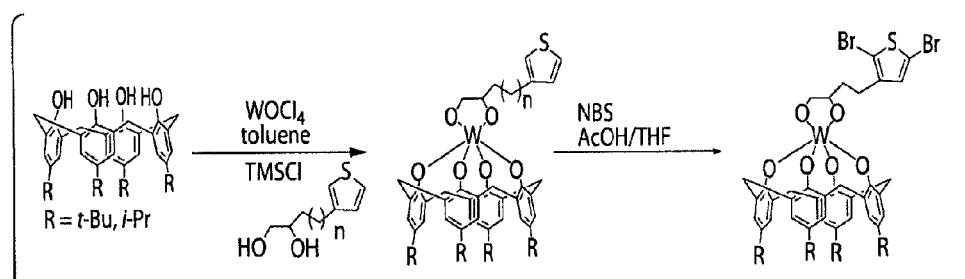
Figure 2E:
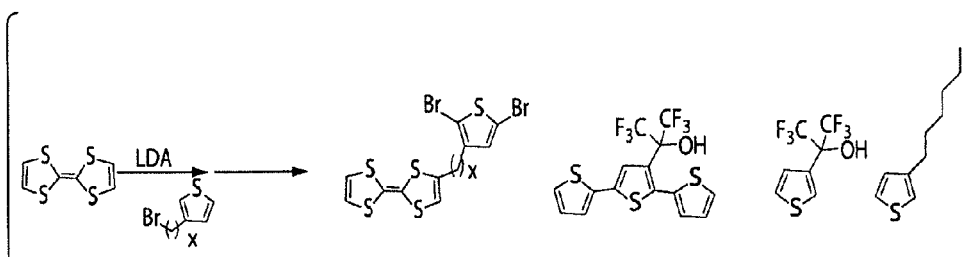
Figure 11A:
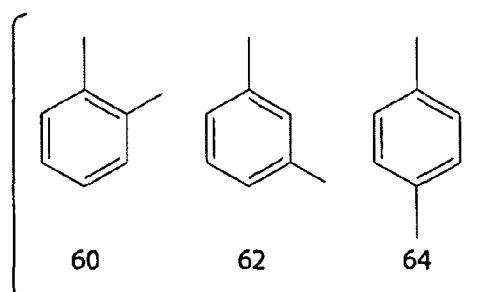
FIG. 11 shows examples of (A) isomers of xylene, (B) various interactions between different isomers of xylenes with a calixarene, and (C) calixarene structures.
Figure 11B:
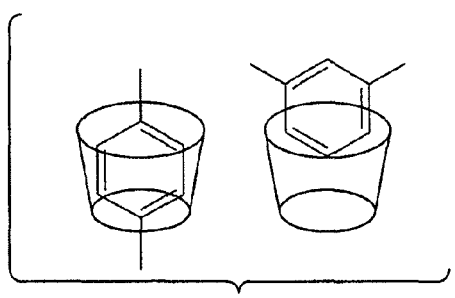
Figure 11C:
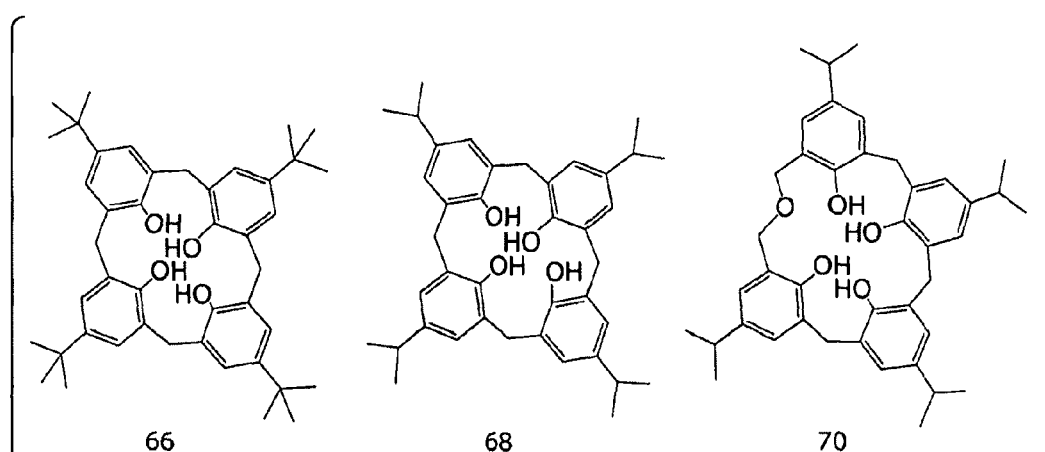
Figure 15A:
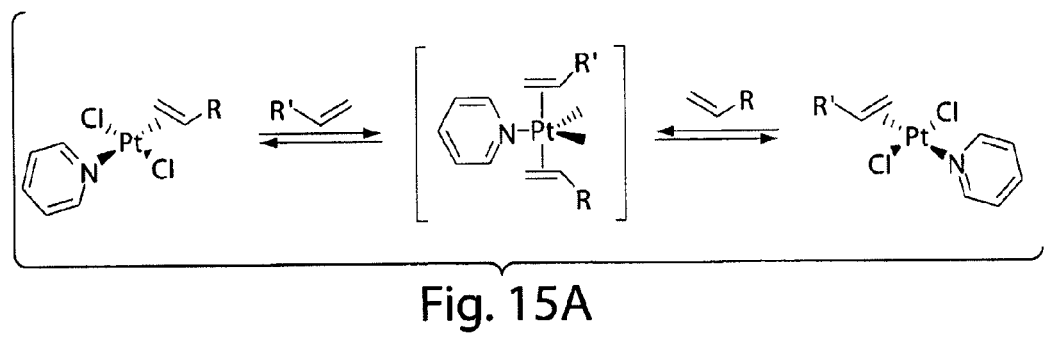
FIG. 15A depicts examples of an olefin associated with a palladium transition metal complex, according to one embodiment of the invention.
Figure 20A:
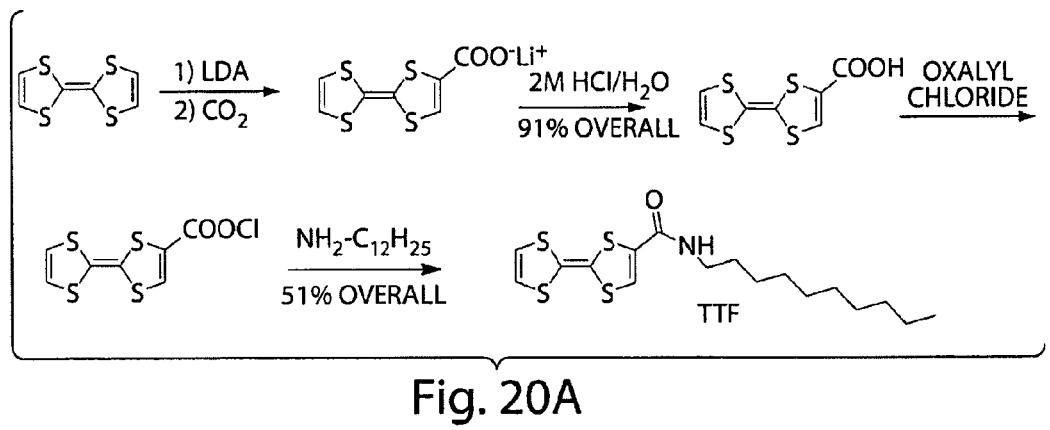
FIG. 20A shows the synthesis of a tetrathiafulvalene (TTF) compound according to one embodiment of the invention.

In some cases, the binding site may comprise a macrocycle, such as a poly(ethylene glycol) macrocycle, a porphyrin macrocycle, or a calixarene macrocycle. In some embodiments, the calixarene receptor may comprise a metal atom, i.e., may be a metal-capped calixarene. In some cases, a calixarene may interact with (e.g., bind) a specific isomer of xylene to a different extent than, i.e., to a greater extent than, other isomers of xylene. In some embodiments, the binding site may comprise a metal complex, such as a transition metal complex. For example, the transition metal complex may be a palladium complex (e.g., $PtCl_2$(ethylene)(pyridine)) that may increase binding efficiency of the sensor material to olefins. In some embodiments, the binding site may be capable of binding an analyte via an interaction that occurs between pairs of biological molecules. Some specific examples of binding sites are shown in FIG. 11C, FIG. 15A, and FIG. 20A. FIG. 2A shows examples of a polymer material (e.g. P3HT) covalently bound to a binding site (e.g., a calixarene, a transition metal complex, a tetrathiafulvalene). Examples of syntheses of substituted polythiophenes are shown in FIG. 2B. FIGS. 2C-2E show examples of the synthesis of a polymer material covalently bound to a transition metal complex, a calixarene, or a tetrathiafulvalene.

In some embodiments, the interaction between the analyte and the binding site may comprise formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), and the like. The interaction may also comprise Van der Waals interactions. In one embodiment, the interaction comprises forming a covalent bond with an analyte. The binding site may also interact with an analyte via a binding event between pairs of biological molecules. For example, the sensor material may comprise an entity, such as biotin, that specifically binds to a complementary entity, such as avidin or streptavidin, associated with a target analyte.

In some cases, the device may comprise additional components or species that may facilitate interaction between the sensor material and analyte, or otherwise enhance performance of the device. In some cases, the additional component may improve the ability of the sensor material to produce a signal or to respond to an analyte. The additional component may associate with the sensor material such that it enhances an electrical, optical, or other property of the sensor material. In some cases, the additional component may act as a dopant for a conductive species (e.g., carbon nanotube) present within the sensor material. For example, the sensor material may comprise a species capable of associating with carbon nanotubes present within the sensor material. In some embodiments, the sensor material includes a species that may interact with the carbon nanotubes via pi-stacking interactions. Examples of such species are shown in FIG. 20A. The additional component may enhance the ability of the sensor material to interact with the analyte via, for example, a charge transfer reaction.

In some embodiments, a device of the present invention may be used as a sensor for determining an analyte. The sensor may comprise additional components, such as a detector component positioned to detect the signal. A "sensor" refers to any device or article capable of detecting an analyte, i.e., by producing a detectable signal (e.g., change of resistance of current flow) upon interaction or reaction of the sensor or a component thereof with the analyte. In one set of embodiments, a device of the present invention may be a chemiresistor device, wherein the device exhibits changes in electrical resistance upon exposure to an analyte. Chemiresistors may be advantageous in that the resistance changes can be read-out by a simple, low power and low current circuit. In other embodiments, a device of the present invention may exhibit signals, or changes in signals, that may be determined using Raman spectroscopy, adsorption and/or emission photophysics, ellipsometry, atomic force microscopy, scanning electron microscopy, electrode passivation, and the like.

Some devices may be fabricated such that two or more different types of analytes present within a sample may be determined. For example, the device may be exposed to a sample which comprises at least two different analytes, wherein the device may comprise components that may specifically interact with each of the two analytes. In some cases, the device may be fabricated such that it includes at least two different types of binding sites, each selected to interact with a particular analyte, such that the different analytes interact specifically with each binding site to produce distinguishable changes to the signal(s) produced by the device. The specific interactions of the different analytes with the device may be determined by observing the change, or lack thereof, in reference signal(s).

In some embodiments, simple screening tests may be conducted to select appropriate sensor materials (e.g., carbon nanotubes, polymer material, etc.), binding sites, device configuration, set of conditions, etc., to suit a particular application. In some cases, a material or device may be screened to determine the sensitivity and/or stability of the material or device. In some cases, a material (and/or device) may be selected based on an ability to detect one or more analytes. For example, the ability of a device to detect an analyte may be determined by comparing the signal (e.g., conductance) of the device prior to and following exposure to an analyte. In another example, a device may be exposed to varying concentrations of an analyte to determine the sensitivity of the device. As another example, a first device and a second device may be provided, wherein the second device comprises a different material (e.g., sensor material, polymer material, electrode material, binding site, etc.) and/or configuration (e.g., relative position of components, or additional component such as a gate electrode or insulating material, etc.) as compared to the first device. Signals produced by the first and second devices prior to and following exposure to an analyte (e.g., percent change in signal upon exposure to the analyte, baseline signal, time required for following exposure to the analyte for the signal to return to baseline, etc.) may then be compared to determine differences between the performance of first and second devices.

In some embodiments, a system comprising two or more devices may be fabricated, wherein each device comprises a first electrode, a second electrode and a sensor material comprising carbon nanotubes. In some cases, the individual devices of the system may be substantially identical. For example, the individual devices may be constructed to interact with the same analyte. In some cases, the individual devices of the system may be different, such that each individual device may selectively interact with a particular analyte present within a sample. This may be accomplished, for example, by fabricating a plurality of devices, each comprising a sensor material and/or binding site responsive to a different analyte. For example, each individual device may be capable of interacting with a particular analyte, and may interact with other analytes to a different (e.g., lesser) extent. This may be useful in determining two or more different types of analytes present in a single sample. For example, the relative concentration of multiple types of analytes present in a single sample may be determined using a system as described herein.

Devices as described herein may have various device configurations, and may be selected to suit a particular application. For example, the sensor material may be fabricated such that a first and the second electrode are in electrochemical communication with the sensor material. "Electrochemical communication," as used herein, refers to materials that are in sufficient communication with each other, such that the transfer of electrons and/or protons can occur between the two materials. For example, the first and second electrodes may not contact one another but may be in electrochemical communication with one another via the sensor material, such that upon application of a voltage between the first and second electrode, a current flows from the one electrode through the sensor material to the other electrode. In some instances, the first electrode may be a source electrode and the second electrode may be a drain electrode. In some instances, the sensor material is placed on a substrate. Non-limiting embodiments of devices are described more fully below.

Figure 3A:
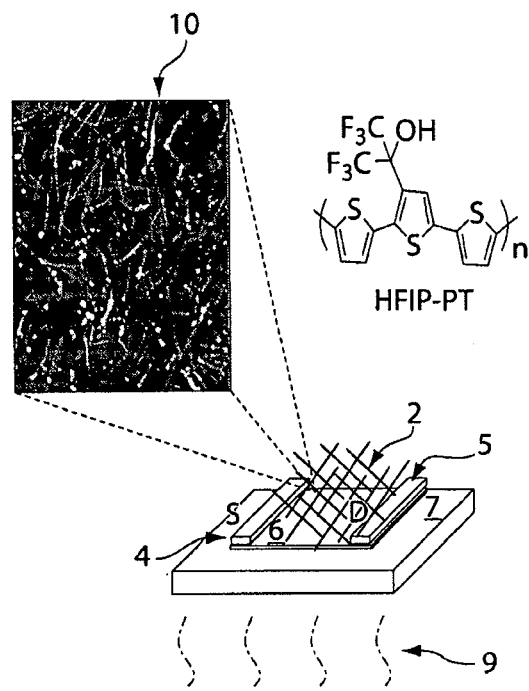
FIG. 3A shows a schematic view of a device, according to one embodiment of the invention.
Figure 3B:
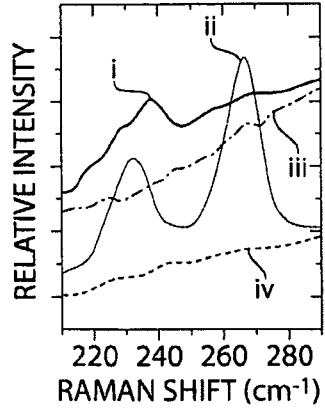
FIG. 3B shows Raman spectra of a sensor material, according to one embodiment of the invention.
Figure 3C:
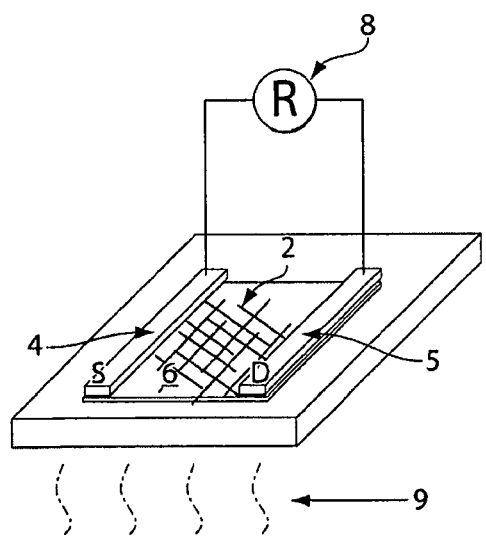
FIG. 3C shows a schematic view of a device, in another embodiment of the invention.

In one embodiment, as shown in FIG. 3A, a device comprises a first electrode 4 formed on a portion of substrate 7. The device also includes a second electrode 5 formed on another portion of substrate 7. The device further comprises sensor material 6, which comprises carbon nanotubes 2, formed on substrate 7 such that sensor material 6 contacts electrode 4 and electrode 6. In operation, the device may be exposed to vapor 9, wherein sensor material 6 interacts with vapor 9 to produce a change in an electrical property of the device, thereby determining analytes present in vapor 9, if any. As shown in FIG. 3C, a voltage may be applied between first electrode 4 and second electrode 5 by connecting the two electrodes with a circuit 8.

Figure 4A:
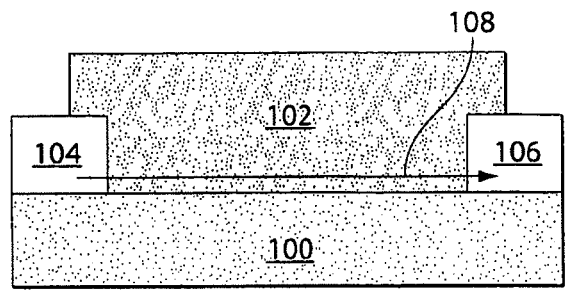
FIGS. 4A-B show examples of various device configurations, according to some embodiments of the invention.
Figure 4B:
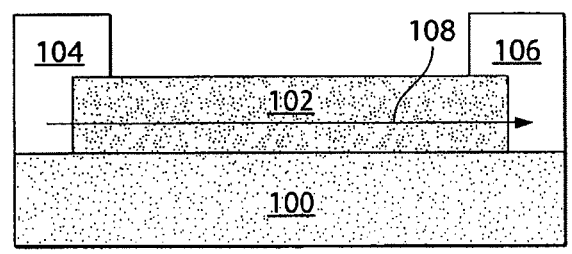

Another embodiment of a device is shown in FIG. 4. Sensor material 102 can be formed on a substrate 100. Source electrode 104 and drain electrode 106 maybe positioned on opposing ends of sensor material 102, such that source electrode 104 and drain electrode 106 contact both sensor material 102 and substrate 100, but do not directly physically contact one another. Source electrode 104 and drain electrode 106 may be in electrochemical communication with sensor material 102, with conductive pathway 108 formed between source electrode 104 and drain electrode 106, through sensor material 102. In some cases, as shown in FIG. 4A, source electrode 104 and drain electrode 106 may be formed on substrate 100, and sensor material 102 may be formed on top of the source electrode 104 and drain electrode 106. In other cases, as shown in FIG. 4B, sensor material 102 may be first formed on substrate 100 followed by deposition of source electrode 104 and drain electrode 106.

Figure 5:
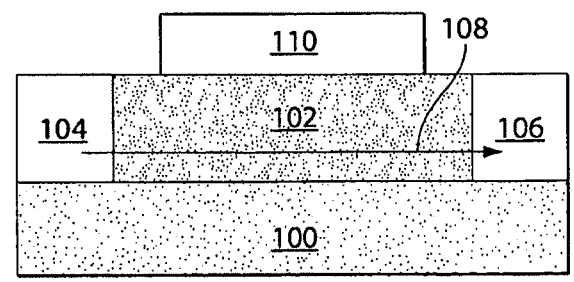
FIG. 5 shows an example of a device configuration, according to one embodiment of the invention.

FIG. 5 illustrates another embodiment of the present invention wherein the device comprises gate electrode 110, which may modulate the current between the source electrode and drain electrode. Source electrode 104 and drain electrode 106 may be formed on opposite ends of sensor material 102, such that source electrode 104 and drain electrode 106 contact both sensor material 102 and substrate 100, but do not directly physically contact one another. Source electrode 104 and drain electrode 106 may also be in electrochemical communication with one another via sensor material 102. Gate electrode 110 may be formed in contact with sensor material 102. In some cases, it may be advantageous to minimize or prevent direct contact between gate electrode 110 and either source electrode 104 or drain electrode 106, or between any two electrodes of the device. A conductive pathway 108 indicates the flow of current between source electrode 104 and drain electrode 106 through sensor material 102. Those of ordinary skill in the art will recognize other possible device configurations, wherein gate electrode 110 may be arranged in various locations, relative to other components of this device. In some cases, more than one gate electrode may be included in the device.

Figure 6A:
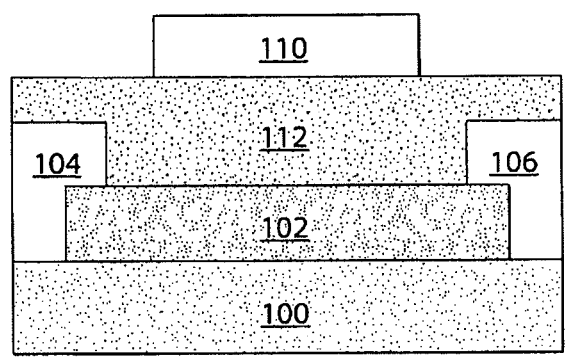
FIGS. 6A-B show examples of various device configurations, according to some embodiments of the invention.
Figure 6B:
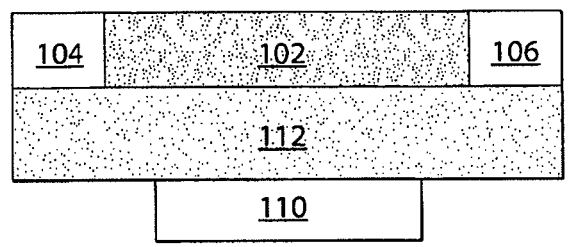

In certain embodiments, the device may further comprise an insulating material. The insulating material may be arranged between the sensor material and one or more electrodes (e.g., gate electrode) and/or the substrate. In some cases, the insulating material may reduce the mobile ion damage and minimize drift in gas sensor devices and/or may improve physical adhesion of the sensor material to the underlying material or substrate. FIG. 6A illustrates an embodiment where both a gate electrode and an insulating material are included in a device. Source electrode 104 and drain electrode 106 may be formed on opposite ends of sensor material 102, such that source electrode 104 and drain electrode 106 contact both the sensor material 102 and substrate 100, but do not directly physically contact one another. Source electrode 104 and drain electrode 106 may be arranged to be in electrochemical communication with one another via sensor material 102. Insulating material 112 may be formed in contact with sensor material 102, and gate electrode 110 may be formed in contact with insulating material 112. Those of ordinary skill in the art will recognize other possible device configurations, wherein insulating material 112 may be arranged in various locations, relative to other components of this device, for example, as shown in FIG. 6B. In some cases, more than one gate electrode and/or insulating material may be included in the device.

It should be understood that the devices may be provided in other, alternative configurations such that the advantages afforded by the present invention are realized. For example, the electrodes may be positioned relative to the sensor material such that, in operation, at least one electronic pathway between the electrodes through the sensor material exists and can be monitored. Similarly, the substrate, gate electrode, and/or other materials can be provided in a wide variety of arrangements, including planar, layered structures, so long as the materials are selected and arranged in relation to each other such that the benefits of the present invention can be realized. Those of ordinary skill in the art would, based on the teachings of the specification, be able to construct devices in alternative arrangements structurally different from those specifically described and illustrated herein.

In certain embodiments, a bias voltage may be applied to the first electrode and/or second electrode to modulate or control the effective resistance of the sensor. In some cases, the bias voltage may be at least about 0.05 volts, at least about 0.1 volts, at least about 0.5 volts, at least about 1 volt, at least about 5 volts, or, in some cases, at least about 10 volts.

In some embodiments, a gate voltage may be applied to the gate electrode to control or modulate the current flow between the first and second electrodes. In some cases, application of a gate voltage may be applied to refresh the device, i.e., to reset the device such that a reference signal, i.e., a signal produced by the device in the absence of analyte, is reestablished or reproduced. Application of the gate voltage may allow for removal of analytes associated with the sensor material (e.g., degassing of the analyte) to refresh or reset the device for subsequent use.

In some cases, application of a gate voltage to the gate electrode may be used to establish a reference signal in the absence of analyte. The device may then be exposed to a sample suspected of containing an analyte while the gate voltage is applied. The signal determined upon exposure to an analyte, if present, may be compared with the reference signal to determine the analyte. In some cases, the gate voltage applied to the device may be at least about −5 volts, at least about −2 volts, at least about −1 volt, at least about about 0.1 volt, at least about 0.1 volt, at least about 1 volt, at least about 2 volts, at least about 5 volts, or in some cases, at least about 10 volts.

Devices of the invention may be fabricated using methods described herein, and/or in combination with other methods known to those of ordinary skill in the art. In some embodiments, methods of the invention may advantageously provide the ability to process materials which may otherwise be insoluble and/or difficult to process. For example, the method may allow for the formation of stable dispersions of carbon nanotubes, such that the carbon nanotubes are readily processable in solution. Some embodiments may include the use of substituted carbon nanotubes, as described more fully below.

In some cases, the method may involve processing a mixture comprising a plurality of carbon nanotubes (e.g., substituted carbon nanotubes) and a polymer material, or precursor thereof, to form a sensor material as described herein. The mixture may be a solution, a suspension, a dispersion, or the like. The mixture may be processed by various methods, including spin coating, drop casting, ink jet printing, electrophoretic deposition, and the like. In some cases, the sensor material may be formed (e.g., deposited) on a substrate, including an electrode, an integrated device, an integrated circuit, or the like.

In some cases, the mixture may be processed to form a thin film comprising the carbon nanotubes and the polymer material. A thin film may have a thickness between about 0.1 nm and about 100 um. For example, the thickness of the film may be less than about 100 um, less than about 50 um, less than about 25 um, less than about 10 um, less than about 5 um, less than about 1 um, less than about 500 nm, less than about 250 nm, less than about 100 nm, less than about 50 nm, less than about 25 nm, less than about 10 nm, less than about 5 nm, less than about 2 nm, less than about 1 nm, less than about 0.5 nm, or in some cases, less than about 0.1 nm. The thickness of the film may or may not be uniform throughout the device. A thin film may be formed using processes such as spin-on methods, chemical vapor deposition, pulsed laser deposition, vacuum plasma spray, wet spray, sputtering, evaporation, or molecular beam epitaxy.

In some embodiments, the sensor material is produced by mixing a polymer material and a plurality of carbon nanotubes and then processing the mixture. In certain embodiments, the polymer material and the carbon nanotubes are mixed with a fluid carrier to form a solution, suspension, dispersion, etc. That is, the polymer material and/or carbon nanotubes may, in some cases, be soluble in a fluid carrier. In some cases, the polymer material and/or carbon nanotubes are not soluble in the fluid carrier. The mixture may comprise any common fluid carrier (e.g., solvent) known to those of common skill in the art such as tetrahydrofuran, chloroform, and the like. In some cases, the solution may comprise more than one fluid carrier.

In some cases, the mixture of the polymer material and the carbon nanotubes may be sonicated to facilitate formation of a dispersion. In certain instances, the mixture may be sonicated for at least about 10 minutes, at least about 30 minutes, at least about 2 hours, at least about 4 hours, at least about 24 hours. The carbon nanotubes may be mixed with the polymer material in at least about 1 wt. %, at least about 10 wt. %, at least about 20 wt. %, at least about 30 wt. %, at least about 40 wt. %, at least about 50 wt. %, at least about 60 wt. %, at least about 70 wt. %, at least about 80 wt. %, at least about 90 wt. %, at least about 99 wt. %, or greater. The mixture of the polymer material and the carbon nanotubes (the sensor material) may be processed by forming a thin film, as discussed more fully below.

Some embodiments include the use of a sensor material comprising binding sites. The binding sites may be present within the sensor material precursor during formation of the sensor material. For example, a plurality of binding sites may be added to a mixture comprising a polymer material and a plurality of carbon nanotubes before formation of the device. In some instances, the plurality of binding sites may be added to the sensor material after formation of the device by, for example, by immersing the device in a solution of the binding sites.

The method may further comprise forming at least one electrode material, for example, on the surface of a substrate or in contact with the sensor material. In some cases, at least two electrode materials, or more, are formed on the surface of a substrate or in contact with the sensor material. The electrode materials, and other components of the device, may be formed at any time during the fabrication process to produce devices as described herein, or devices having an alternative arrangement. For example, the sensor material, electrode materials(s) (e.g., source electrode, drain electrode, gate electrode, etc.), and/or insulating material may be fabricated in any order to produce a device as described herein. In some embodiments, the electrode material may be formed on a substrate prior to formation of the sensor material. In some embodiments, the electrode may be formed on the sensor material. The electrode material(s) may be deposited onto any component of the device using methods known in the art, such as electroplating. In some instances, the integrated device may be incorporated into a wireless sensory network.

As described herein, one or more analytes may be determined by determining a change in a signal of the device. The signal may comprise an electrical signal (e.g. conductance, voltage, resistance, current, etc.), optical signal (e.g., fluorescence, luminescence, color, etc.), mechanical signal (e.g., hardness, etc.), and/or the like. The change in signal may be determined using various techniques. For example, a change in an electrical signal may be determined by monitoring the current, voltage, and/or resistance of the device. In one embodiment, the signal comprises an electrical signal, such as resistance. In some cases, the signal may comprise a change (e.g., increase, decrease) in resistance of a current flow through the device. In some embodiments, the change in signal may comprise a change in the conductance of the device. In some instances, the change in the signal may comprise a change in the fluorescence or emission of the device. In some cases, upon exposure of the device to an analyte, a signal of the device may increase or decrease by at least about 5%, at least about 10%, at least about 20%, at least about 30%, at least about 40%, at least about 50%, at least about 60%, at least about 70%, at least about 80%, at least about 90%, at least about 100%, or more.

In some cases, when the analyte is present in an amount equal to or less than about 1.0 ppm, a change in the resistance of the device comprises a change of at least about 1%. In some cases, when the analyte is present in an amount equal to or less than about 0.1 ppm, the change in resistance of the device comprises a change of at least about 1%. In some cases, when the analyte is present in an amount equal to or less than about 5 ppb, less than about 10 ppb, less than about 0.6 ppm, less than about 1.0 ppm, less than about 2.0 ppm, less than about 3.0 ppm, less than about 5.0 ppm, or less than about 10 ppm, the change in resistance of the device comprises a change of at least about 1%, at least about 2%, at least about 3%, at least about 5%, at least about 10%, at least about 20%, at least about 30%, at least about 40%, at least about 50%, or more.

In some cases, the analyte may produce a colorimetric change within the device, wherein observation of a visible change in color may determine the analyte. In some embodiments, the analyte may produce a change in an absorption or luminescence spectrum of the device. In such cases, the change in a peak and/or trough of the spectrum may be measured, for example, by addition, subtraction, multiplication, or division of the spectra, or by observation of a change in the distance between peaks and/or troughs of the spectra, a change in the shape of the spectra, and/or the like. In some cases, the change in signal may be determined using an analyzer that may compare the signals produced by the device before and after exposure to an analyte. In some cases, the signals may be further processed to determine the analyte. For example, the signal may be filtered, amplified, subject to Fourier transforms, decomposed using wavelet decomposition, and/or the like.

As noted above, devices of the invention may include one or more binding sites. The binding site may be any moiety that may interact with an analyte, and may be incorporated within the device in various configurations. For example, the binding sites may be attached a portion of the sensor material via a bond. In some cases, the binding sites may be attached to a polymeric material via a bond. In some cases, the binding sites may be attached to a conductive species (e.g., carbon nanotube) via a bond. In some cases, the binding sites may be substantially contained within (e.g., dispersed within) the sensor material, and may not form a covalent bond to a carbon nanotube or polymer material. The binding site may comprise a biological or a chemical group capable of binding another biological or chemical molecule in a medium (e.g., solution, vapor phase, solid phase). For example, the binding site may be a functional group, such as a thiol, aldehyde, ester, carboxylic acid, hydroxyl, and the like, wherein the functional group forms a bond with the analyte. In some cases, the binding site may be an electron-rich or electron-poor moiety wherein interaction between the analyte and the moiety comprises an electrostatic interaction. Examples of binding sites include fluorinated alcohols, calixarenes, and the like. A non-limiting example of a binding site that may be employed within the sensor material includes hexafluoroisopropanol groups, which may, in some cases, facilitate interaction between the sensor material and analytes which comprise phosphate esters (e.g., chemical warfare agents such as sarin gas).

In some embodiments, the binding site may be capable of binding an analyte via an interaction that occurs between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/ antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Specific non-limiting examples of binding sites include peptides, proteins, DNA, RNA, PNA.

As used herein, the term "carbon nanotube" is given its ordinary meaning in the art and refers to a substantially cylindrical molecule, in some cases, comprising a fused network of six-membered aromatic rings. In some cases, carbon nanotubes may resemble a sheet of graphite rolled up into a seamless cylindrical structure. It should be understood that the carbon nanotube may also comprise rings other than six-membered rings. Typically, at least one end of the carbon nanotube may be capped, i.e., with a curved or nonplanar aromatic group. Carbon nanotubes may have a diameter of the order of nanometers and a length on the order of millimeters, resulting in an aspect ratio greater than about 100, greater than about 1000, greater than about 10,000, or greater. The term "carbon nanotube" includes single-walled nanotubes (SWCNTs), multi-walled nanotubes (MWCNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube).

The carbon nanotubes may be functionalized or substituted with a wide range of functional groups. Examples of functional groups that carbon nanotubes may be substituted with include peptides, proteins, DNA, RNA, peptide nucleic acids (PNA), metal complexes, ligands for metals, ligands for proteins, antibodies, polarizable aromatics, crown ethers, hydroxyl amines, polymers, initiators for polymerizations, liquid crystals, fluorocarbons, synthetic receptors, and the like. The properties of the carbon-containing molecules may also be tailored based on the substitution of the fused, aromatic network. Those skilled in the art would recognize what types of functional groups would afford a particular, desired property, such as increased solubility, or the ability to determine an analyte. In some embodiments, the substituted carbon nanotube comprises a binding site. In some embodiments, substituted carbon nanotubes may be readily processed in a fluid carrier. That is, dispersions of substituted carbon nanotubes may be formed.

In some embodiments, the substituted carbon nanotube may have the formula,

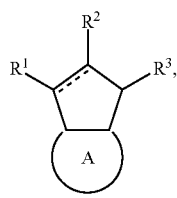

wherein A is a carbon nanotube; $R^1$, $R^2$, and $R^3$ can be the same or different and each is an atom or a chemical group; and ═ is a single bond or double bond. In one set of embodiments, A is a single-walled carbon nanotube. In one set of embodiments, A is a multi-walled carbon nanotube. In some cases, $R^1$, $R^2$, and $R^3$ can be ═O, hydroxy, halide, alkyl, heteroalkyl, alkenyl, heteroalkenyl, alkynyl, heteroalkynyl, aryl, or heteroaryl, optionally substituted. In the structure above, the five membered carbon ring may be fused to A via two atoms of A, such that the structure comprises a group,

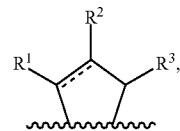

wherein "⁓⁓⁓" comprises a nonplanar aromatic portion of the carbon nanotube. The two atoms may be ring atoms of at least two aromatic rings of the fused network. In some embodiments, the compound may comprise the structure,

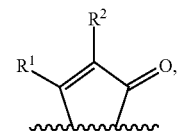

wherein $R^1$ is an ester and $R^2$ is a leaving group. $R^1$ may be an acid chloride, carboxylic acid or salt thereof, ester, amide, or substituted derivative thereof.

In some embodiments, $R^1$ has the structure,

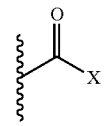

wherein X is H, OH, halide, alkyl, heteroalkyl, alkenyl, heteroalkenyl, alkynyl, heteroalkynyl, aryl, heteroaryl, or salt thereof, optionally substituted; $R^2$ is a is an atom or chemical group that is capable of being replaced or altered; and $R^3$ is ═O, ═S, or ═NR$^4$. $R^1$ can be an acid chloride, carboxylic acid or salt thereof, ester, amide, other carbonyl groups or substituted derivative thereof $R^{1-3}$ may comprise atoms or chemical groups that can be transformed into other functional groups by known methods, including organic transformations known to those of ordinary skill in the art. In some cases, any one of $R^{1-3}$ may be a leaving group. As used herein, a "leaving group" is given its ordinary meaning in the art of synthetic organic chemistry and refers to an atom or a group capable of being displaced by a nucleophile. Examples of suitable leaving groups include, but are not limited to, halides (such as chloride, bromide, and iodide), alkanesulfonyloxy, arenesulfonyloxy, alkyl-carbonyloxy (e.g., acetoxy), arylcarbonyloxy, mesyloxy, tosyloxy, trifluoromethane-sulfonyloxy, aryloxy, methoxy, N,O-dimethylhydroxylamino, pixyl, and the like. In some cases, the leaving group is an aryloxy group substituted with an electron-withdrawing group (e.g., 2,-nitrophenoxy, 2,4-dinitrophenoxy).

In some embodiments, the substituted carbon-containing molecule may have the structure,

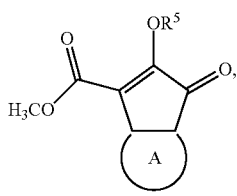

wherein $R^5$ is alkyl, heteroalkyl, alkenyl, heteroalkenyl, alkynyl, heteroalkynyl, aryl, heteroaryl, or a salt thereof, optionally substituted.

In some embodiments, $R^1$, $R^2$, and/or $R^3$ may be joined to form a ring. For example, any two of $R^1$, $R^2$, and $R^3$ may be joined to form a ring. The ring may comprise any number of ring atoms and may include carbon atoms, heteroatoms, metals, and the like. The ring may also be optionally substituted, as described herein. In some embodiments, $R^1$ and $R^3$ may be joined to form a ring comprising at least six ring atoms.

Some embodiments of the invention may comprise at least two or more functional groups fused to the substituted carbon nanotube. In some cases, the two or more functional groups may be joined by a linker. The substituted carbon nanotube may comprise at least two groups having the formula,

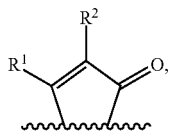

wherein $R^1$ of each functional group is joined by a linker. The linker may be a flexible linker such as an alkyl or heteroalkyl group, or the linker may be a rigid linker, such as an aryl, heteroaryl, alkene, heteroalkene, alkyne, or heteroalkene group. For example, the linker may be a phenyl, pyridinyl, pyrrolyl, thiophenyl, furanyl, biphenyl, or iptycenyl group, a tartrate ester, an acetylene, an alkene, combinations thereof, or the like. In some cases, the linker may be covalently bonded to the functional groups. In some cases, the linker may be non-covalently bonded to the functional groups. Examples of non-covalent bonds include ionic bonds, hydrogen bonds (e.g., between hydroxyl, amine, carboxyl, thiol and/or similar functional groups, for example), dative bonds (e.g. complexation or chelation between metal ions and monodentate or multidentate ligands), or the like. Non-covalent bonds may also comprise Van der Waals interactions.

The functional groups on the carbon nanotubes may be further reacted to replace an atom or group, or to attach additional atoms or groups. For example, the functional group may comprise a carbon-carbon triple bond that may be readily modified using "click chemistry" (e.g., 1,3-dipolar cycloaddition reactions). That is, the carbon-carbon triple bond may be reacted with a species comprising an azide via a 1,3-dipolar cycloaddition to form a triazole ring that is covalently bound to the functional group of the carbon nanotube and the species. Those of ordinary skill in the art would be able to select the appropriate reaction conditions and additives suitable for a particular 1,3-dipolar cycloaddition reaction. Methods for performing 1,3-dipolar cycloaddition reactions are also described, for example, in *Synthetic Applications of 1,3-Dipolar Cycloaddition Chemistry Toward Heterocycles and Natural Products*, A. Padwa, W. H. Pearson, Wiley-Interscience, 2002, the contents of which are incorporated herein by reference.

Substituted carbon nanotubes may be synthesized using various methods. In some embodiments, the method may comprise reacting an alkyne, a carbon-containing molecule, and a nucleophile to produce a substituted carbon-containing molecule, as described in Zhang et al., J. Am. Chem. Soc. 2007, 129(25), 7714, incorporated herein by reference. Other methods are described in PCT Publication No. WO2008/133779 by Swager, et al. For example, as shown in Scheme 1 below, an alkyne, a carbon-containing molecule, and a nucleophile may react to form a product comprising at least a portion of each component (e.g., alkyne, carbon-containing molecule, and nucleophile) covalently bound to one another. As used herein, the term "react" or "reacting" refers to the formation of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s). A "stable, isolable compound" refers to isolated reaction products and does not refer to unstable intermediates or transition states. A variety of functional groups may be installed on the carbon-containing molecule by varying the alkyne (e.g., electrophile) and nucleophile.

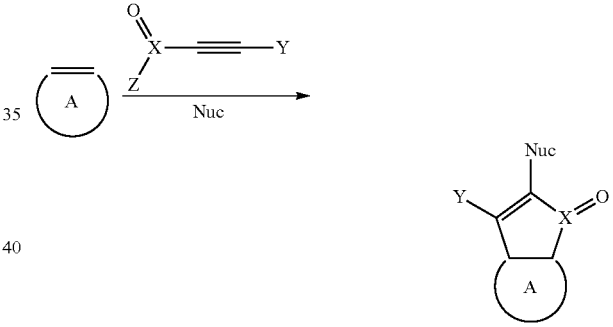

Scheme 1

Polymers or polymer materials, as used herein, refer to extended molecular structures comprising a backbone (e.g., non-conjugated backbone, conjugated backbone) which optionally contain pendant side groups, where "backbone" refers to the longest continuous bond pathway of the polymer. In one embodiment, at least a portion of the polymer is conjugated, i.e. the polymer has at least one portion along which electron density or electronic charge can be conducted, where the electronic charge is referred to as being "delocalized." A polymer may be "pi-conjugated," where atoms of the backbone include p-orbitals participating in conjugation and have sufficient overlap with adjacent conjugated p-orbitals. In one embodiment, a substantial majority of the backbone is conjugated and the polymer is referred to as a "pi-conjugated polymer" or "conjugated polymer." Polymers having a conjugated pi-backbone capable of conducting electronic charge may be referred to as "conducting polymers." In some cases, the conjugated pi-backbone may be defined by a plane of atoms directly participating in the conjugation, wherein the plane arises from a preferred arrangement of the p-orbitals to maximize p-orbital overlap, thus maximizing conjugation and electronic conduction. In some cases, the pi-backbone may preferably have a non-planar or twisted ground state conformation, leading to decreased conjugation and a higher energy conduction band. It should be understood that other types of conjugated polymers may be used, such as sigma-conjugated polymers.

In one embodiment, the polymer is selected from the group consisting of polyarylenes, polyarylene vinylenes, polyarylene ethynylenes and ladder polymers, i.e. polymers having a backbone that can only be severed by breaking two bonds. Examples of such polymers include polythiophene, polypyrrole, polyacetylene, polyphenylene and substituted derivatives thereof. In certain cases, the polymer may be a copolymer of polythiophene. In some embodiments, the polymer may include poly(3-hexylthiophene) and/or hexafluoroisopropanol substituted polythiophene.

The polymer can be a homo-polymer or a co-polymer such as a random co-polymer or a block co-polymer. In one embodiment, the polymer is a block co-polymer. An advantageous feature of block co-polymers is that they may mimic a multi-layer structure, wherein each block may be designed to have different band gap components and, by nature of the chemical structure of a block co-polymer, each band gap component is segregated. As described herein, the band gap and/or selectivity for particular analytes can be achieved by modification or incorporation of different polymer types. The polymer compositions can vary continuously to give a tapered block structure and the polymers can be synthesized by either step growth or chain growth methods.

The number average molecular weight of the polymer may be selected to suit a particular application. As used herein, the term "number average molecular weight ($M_n$)" is given its ordinary meaning in the art and refers to the total weight of the polymer molecules in a sample, divided by the total number of polymer molecules in a sample. In some cases, the performance and/or stability of a sensor material comprising a polymer may be enhanced by incorporation of a higher molecular weight polymer, i.e., a polymer having a number average molecular weight of at least about 25,000, at least about 50,000, at least about 70,000, at least about 100,000, or greater. Those of ordinary skill in the art will be able to select methods for determining the number average molecular weight of a polymer, for example, gel permeation chromatography (GPC). In some cases, the GPC may be calibrated vs. polystyrene standards. In some cases, the number average molecular weight of the polymer is at least about 10,000, at least about 20,000, at least about 25,000, at least about 35,000, at least about 50,000, at least about 70,000, at least about 75,000, at least about 100,000, at least about 110,000, at least about 125,000, or greater.

Figure 7:
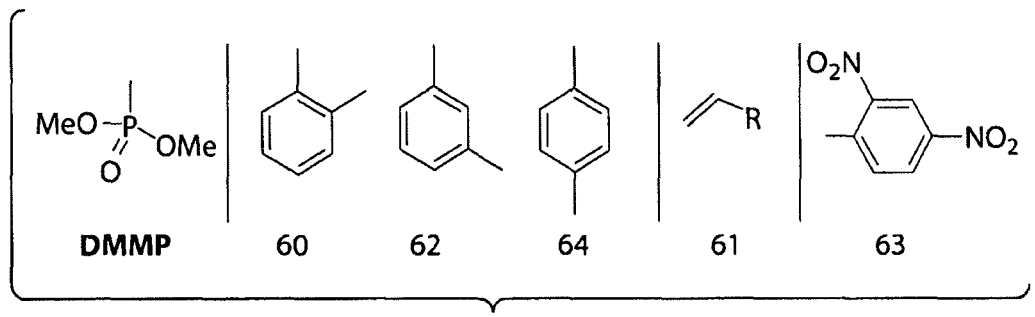
FIG. 7 shows various analytes that may be determined using a device, according to some embodiments of the present invention.

As used herein, an "analyte" can be any chemical, biochemical, or biological entity (e.g. a molecule) to be analyzed. The analyte may be a chemical or biological analyte. In some cases, the sensor material may be selected to have high specificity for the analyte, and may be a chemical, biological, or explosives sensor, for example. In some embodiments, the analyte comprises a functional group that is capable of interacting with at least a portion of the sensor material (e.g., a binding site). In some cases, the sensor material may determine changes in pH, moisture, temperature, and the like, of a surrounding medium. In a specific example, the analytes are chemical warfare agents (e.g., sarin gas) or analogs of chemical warfare agents (e.g., dimethyl methylphosphonate, DMMP). Other specific examples of analytes are olefins, nitric oxide, thiols, thioesters, amines, and the like. FIG. 7 shows some specific analytes including DMMP, o-xylene (60), m-xylene (62), p-xylene (64), olefinic compounds (61), and nitroaromatic compounds (63).

In some embodiments, various components of the device are formed on a substrate. The substrate can comprise a wide variety of materials, as will be appreciated by those in the art, including printed circuit board (PCB) materials. Suitable substrates include, but are not limited to, fiberglass, Teflon, ceramics, glass, silicon, mica, plastic (including acrylics, polystyrene and copolymers of styrene and other materials, polypropylene, polyethylene, polybutylene, polycarbonate, polyurethanes, and derivatives thereof, etc.), GETEK (a blend of polypropylene oxide and fiberglass), and the like.

As mentioned above, the device may comprise an insulating material. Examples of suitable insulating materials include, but are not limited to, polysilicate glass, silicon dioxide, silicon nitride, and the like.

As used herein, the term "electrode" or "electrode material" refers to a composition, which, when connected to an electronic device, is able to sense a current or charge and convert it to a signal. An electrode may be comprised of a conductive material or combination of materials such as, for example, metals. Non-limiting examples of suitable metals include gold, copper, silver, platinum, nickel, cadmium, tin, and the like. The electrodes may also be any other metals and/or non-metals known to those of ordinary skill in the art as conductive (e.g. ceramics). The electrodes may be deposited on a surface via vacuum deposition processes (e.g., sputtering and evaporation) or solution deposition (e.g., electroplating or electroless processes). In a specific example, gold electrodes are deposited by sputter-coating.

As used herein, the term "sample" refers to any medium (e.g., solid, liquid, gas) that can be evaluated in accordance with the invention including, such as air or other vapor samples, soil, water, a biological sample, etc. A "sample suspected of containing" a particular component means a sample with respect to which the content of the component is unknown. For example, a soil sample suspected of having one or more explosive agents, but not known to have the explosive agent, defines a sample suspected of containing an explosive agent. "Sample" in this context includes naturally-occurring samples, such as soil samples, water samples, air samples, samples from food, livestock, plants, etc.

As used herein, the term "alkyl" is given its ordinary meaning in the art and may include saturated aliphatic groups, including straight-chain alkyl groups, branched-chain alkyl groups, cycloalkyl(alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. In some embodiments, an alkyl group may be a lower alkyl group, wherein a lower alkyl group comprises 10 or fewer carbon atoms in its backbone (e.g., $C_1$-$C_{10}$ for straight chain lower alkyls).

The term "heteroalkyl" is given its ordinary meaning in the art and refers to alkyl groups as described herein in which one or more atoms is a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" is given its ordinary meaning in the art and refers to single-ring aromatic groups such as, for example, 5-, 6- and 7-membered single-ring aromatic groups. The term "heteroaryl" is given its ordinary meaning in the art and refers to aryl groups as described herein in which one or more atoms is a heteroatom (e.g., oxygen, nitrogen, sulfur, and the like).

Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. It should be understood that, when aryl and heteroaryl groups are used as ligands coordinating a metal center, the aryl and heteroaryl groups may have sufficient ionic character to coordinate the metal center. For example, when a heteroaryl group such as pyrrole is used as a nitrogen-containing ligand, as described herein, it should be understood that the pyrrole group has sufficient ionic character (e.g., is sufficiently deprotonated to define a pyrrolyl) to coordinate the metal center. In some cases, the aryl or heteroaryl group may comprise at least on functional group that has sufficient ionic character to coordinate the metal center, such as a biphenolate group, for example.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiocarbonyl" group. Where W is a S-alkyl, the formula represents a "thioester." Where W is SH, the formula represents a "thiol-carboxylic acid." On the other hand, where W is alkyl, the above formula represents a "ketone" group. Where W is hydrogen, the above formula represents an "aldehyde" group.

As used herein, the term "halogen" or "halide" designates —F, —Cl, —Br, or —I.

The term "alkoxy" refers to the group, —O-alkyl.

The term "aryloxy" refers to the group, —O-aryl.

The term "acyloxy" refers to the group, —O-acyl.

The term "arylalkyl", as used herein, refers to an alkyl group substituted with an aryl group.

The terms "amine" and "amino" are art-recognized and refer to both unsubstituted and substituted amines, e.g., a moiety that can be represented by the general formula: N(R') (R'')(R''') wherein R', R'', and R''' each independently represent a group permitted by the rules of valence.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For example, a substituted alkyl group may be $CF_3$. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

EXAMPLES

All chemicals were of reagent grade from Sigma-Aldrich and used as received. Single-walled carbon nanotubes were acquired from Carbon Nanotechnologies Inc. (CNT lot #R0204) and were synthesized by the high-pressure catalytic decomposition of carbon monoxide (HIPCO) method.

NMR spectra were obtained on Varian Mercury (300 MHz). NMR chemical shifts are referenced to $CHCl_3$/TMS (7.27 ppm for $^1H$, 77.23 ppm for $^{13}C$). For $^{19}F$ NMR spectra, trichlorofluoromethane was used as an external standard (0 ppm), and upfield shifts are reported as negative values. In some cases, signals associated with the $CF_3$ groups and proximal quaternary centers were not reported in the $^{13}C$ NMR spectra due to C-F coupling and low signal-to-noise ratios. High-resolution mass spectra (HRMS) were obtained using a peak-matching protocol to determine the mass and error range of the molecular ion. Fourier Transform infrared (FT-IR) spectroscopy was performed on a Perkin-Elmer model 2000 FT-IR spectrophotometer using the Spectrum v. 2.00 software package. Polymer molecular weights were determined at room temperature on a HP series 1100 GPC system in THF at 1.0 mL/min (1 mg/mL sample concentrations). UV/V is spectra were recorded on an Agilent 8453 diode-array spectrophotometer. Emission spectra were acquired on a SPEX Fluorolog fluorometer (model FL-321, 450 W xenon lamp) using either right-angle detection (solution measurements) or front-face detection (thin-film measurements). Melting points were measured with a Meltemp II apparatus and are reported uncorrected. The source drain current dependence on gate voltage was measured with a Keithley 4200 semiconductor characterization system. Raman spectra were measured with a Kaiser Hololab 5000R Modular Research Raman Spectrometer with Microprobe from MIT Center for Materials Science and Engineering.

Example 1

The following example describes the use of a sensor material including SWCNTs dispersed with a hexafluoroisopropanol functionalized polythiophene in the fabrication of a highly sensitive and selective chemiresistor sensor.

Stable dispersions of single walled CNTs (SWCNTs) were prepared by sonicating the SWCNTs in the presence 50 wt. % of a hexafluoroisopropanol substituted polythiophene (HFIP-PT) or poly(3-hexylthiophene) (P3HT). Polymer/SWCNT films (50 nm thick) were spin-coated from 0.2 wt. % solutions (THF for HFIP-PT and CHCl$_3$ for P3HT) onto a glass substrate, and two gold strip electrodes (50 nm thick) were then sputter-coated onto the film. The resistance of HFIP-PT/SWCNT devices ranged from 0.5 to 1.5 MΩ. The quality of the dispersions may indicate that the CNTs form a percolative network of largely individual tubes.

A schematic view of the device is shown in FIG. 3A, wherein the device comprises a percolative network of carbon nanotubes 2 positioned between two gold electrodes 4 deposited by drop casting a HFIP-PT stabilized dispersion 6. The source-drain dimension was 5 mm×5 mm. FIG. 3A shows an AFM image (10) of the SWCNT network (3 μm×3 μm), wherein the SWCNTs were observed to be well-dispersed by HFIP-PT. FIG. 3B shows the radical breathing Raman modes of SWCNTs taken from tubes (i) suspended by HFIP-PT in THF, and then (ii) as a dried, drop cast HFIP-SWCNT dispersion. FIG. 3B shows additional curves for HFIP-PT without SWCNTs (iii) in a solution and (iv) as a solid. The excitation wavelength was 785 nm. The low intensity of the (10, 2)-radical breathing Raman mode (RBM) at 264 cm$^{-1}$ in FIG. 3B demonstrated a decrease in the amount of SWCNT bundles when dispersed by HFIP-PT.

The HFIP group associated with the polythiophene may be useful as it is able to hydrogen bond with phosphate esters that are common to a number of chemical warfare agents such as sarin gas. Due to the similar hydrogen bonding characteristics and vapor pressure (160 Pa at 25° C.) of dimethyl methylphosphonate (DMMP) to chemical warfare agents, many of the presented measurements were obtained using DMMP, a less toxic stimulant. The sensory response investigated was a conductance measurement between the two electrodes at a constant bias voltage (0.1 V). Chemiresistors based on an HFIP-PT/SWCNT hybrid system were shown to be highly sensitive and selective for DMMP.

Figure 8:
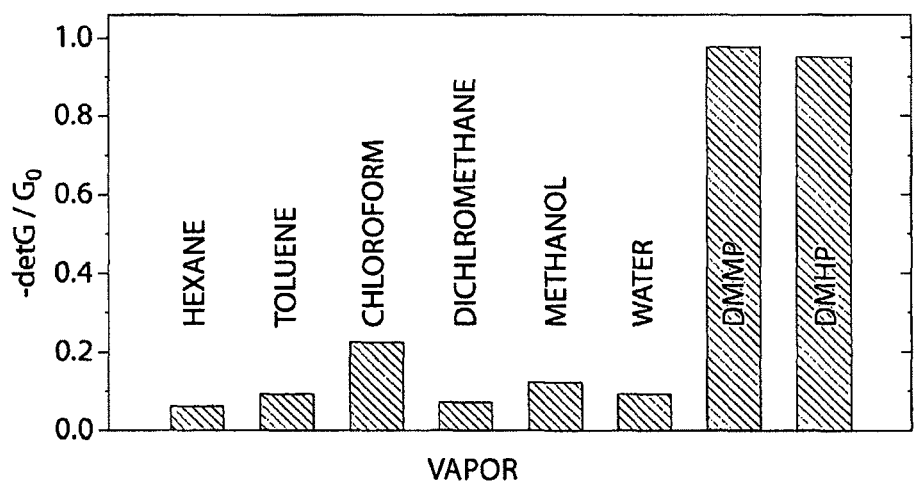
FIG. 8 shows a graph of the conductance change of a device upon exposure to various analytes, according to one embodiment of the present invention.
Figure 9A:
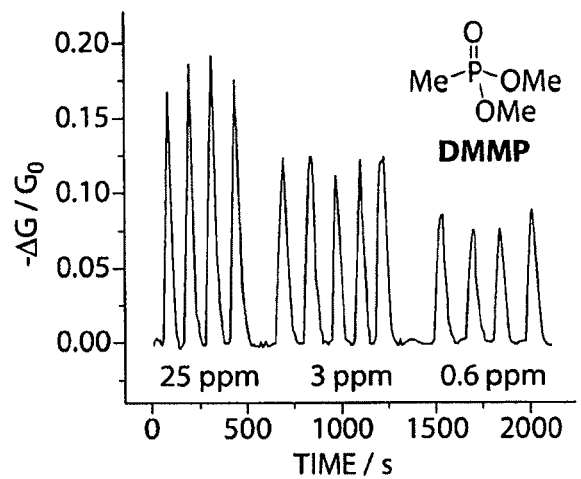
FIG. 9A shows a graph of the conductance change of a device as a function of time in one embodiment of the invention, when exposed to varying concentrations of dimethyl methylphosphonate (DMMP).
Figure 9B:
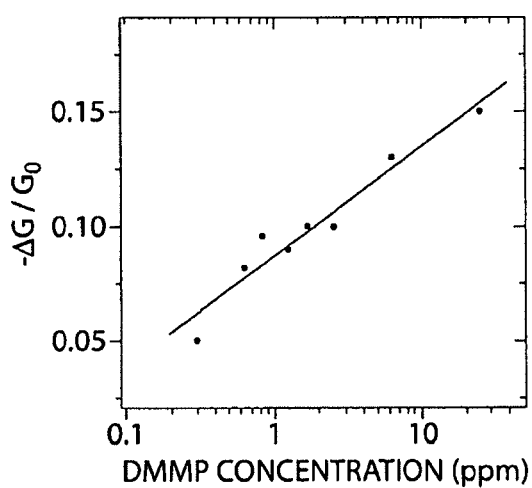
FIG. 9B shows a calibration curve of the conductance change observed for a device as a function of DMMP concentration.

FIG. 8 shows the conductance change of the HFIP-PT/SWCNT sensor in response to common organic solvents, DMMP, and dimethyl phosphite (DMHP) under saturated vapor conditions. FIG. 9A shows the conductance change ($-\Delta G/G_0$) of the HFIP-PT/SWCNT sensor upon exposure to varying concentrations of DMMP. The bias voltage was fixed at 0.1 V, and the temperature was 70° C. As depicted by the graph shown in FIG. 9A, the sensor response was fast and reproducible even at low analyte concentrations. For instance, an 8% conductance change upon exposure to 0.6 ppm of DMMP was obtained. A conductance change of 1% was observed in response to 0.05 ppm DMMP, which qualifies the sensor at a ppb level sensing. FIG. 9B shows the calibration curve of the sensor at DMMP concentration of 0.3-25 ppm. This curve shows that the sensor displays a linear logarithmic response to analyte concentration over two decades of concentration.

Figure 9C:
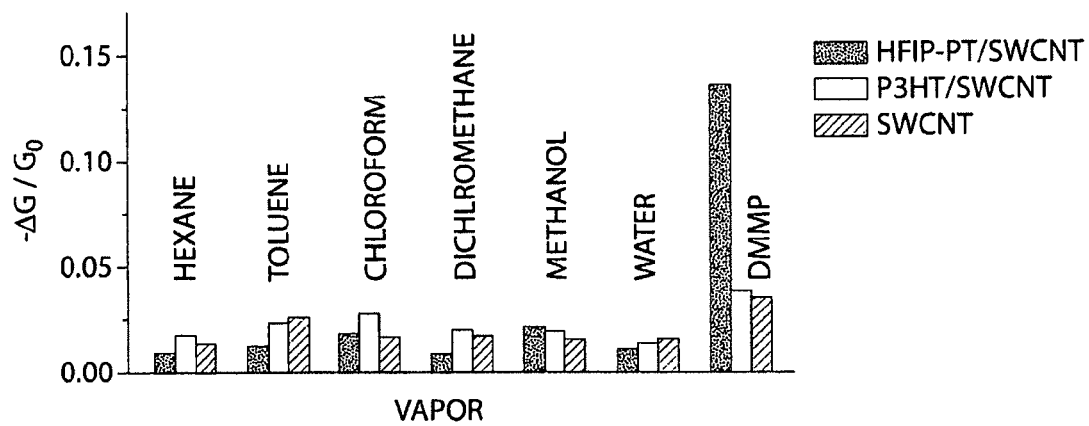
FIG. 9C shows graphs of the conductance change of devices to various analytes, according to some embodiments of the invention.

FIG. 9C shows the conductance change of three different sensors in response to common organic solvents and DMMP diluted to 1% of saturated vapor conditions at room temperature, with a bias voltage fixed at 0.1 V. In FIG. 9C, HFIP-PT/SWCNT refers to a sensor including SWCNTs and a HFIP-PT polymer; P3HT/SWCNT refers to a sensor including SWCNTs and a P3HT polymer; and SWCNT refers to a sensor including SWCNTs. The selectivity and sensitivity for SWCNTs deposited from polymer stabilized dispersions and non-stabilized dispersions can be compared using this plot. The relative responses are for 1% of the equilibrium vapor pressures. The equilibrium vapor pressure of methanol (167,000 ppm) is more than 100 times that of DMMP (1,600 ppm), therefore, the sensitivity of the experiment was high. Moreover, the hydrogen bonding ability of HFIP-PT/SWCNTs increased the response and selectivity for DMMP, as compared to P3HT/SWCNTs and bare SWCNTs. The enhancement due to the HFIP-PT at low analyte concentrations was significant. At equilibrium vapor pressures of DMMP, the HFIP-PT/SWCNT sensor gave only approximately 40% larger response than the P3HT/SWNCT, whereas at 1 ppm of DMMP the HFIP/SWCNT was nine times more sensitive.

Figure 10A:
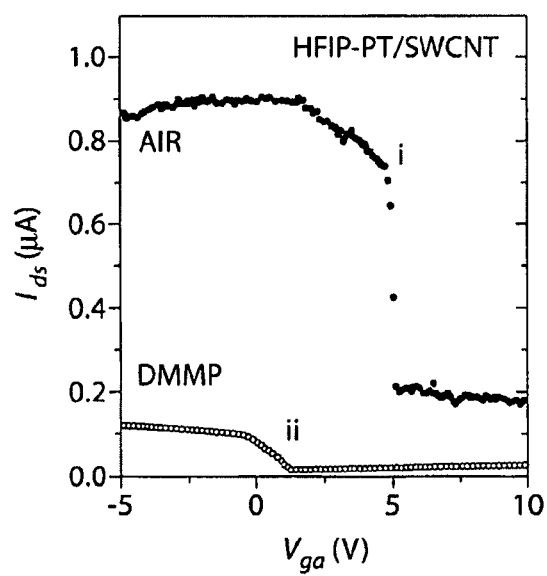
FIG. 10A shows a graph of source-drain current versus gate voltage for a device under an atmosphere of (i) air, or (ii) analyte.
Figure 10B:
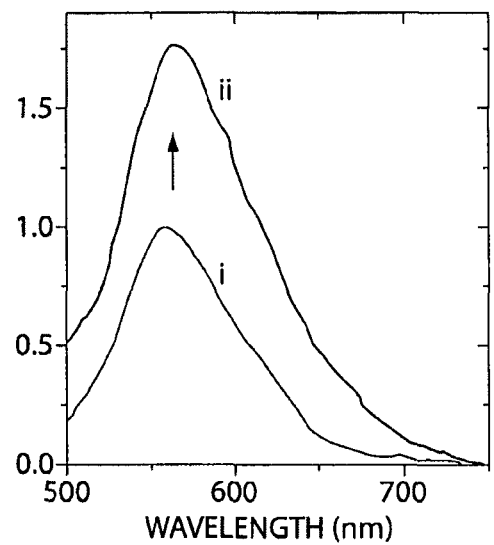
FIG. 10B shows a graph of fluorescence emission of a sensor material under an atmosphere of (i) air, or (ii) analyte.
Figure 10C:
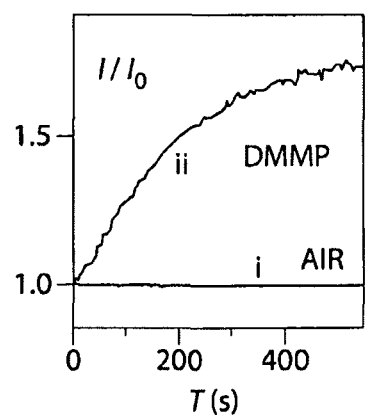
FIG. 10C shows a graph of the fluorescence intensity change versus exposure time of a sensor material under an atmosphere of (i) air, or (ii) analyte.

To explore the mechanism of the DMMP response in the HFIP-TP/SWCNT sensor, sensory studies were performed in a field effect transistor architecture. FIG. 10A shows the source-drain current versus the gate voltage of the sensor under conditions of (i) air and (ii) saturated DMMP vapors. The source-drain bias voltage was fixed at 1 mV. The gate voltage was scanned from 10 V to −5 V. An excitation wavelength of 450 nm was used. FIG. 10B shows the fluorescent emission of the HFIP-PT/SWCNT film under (i) air and (ii) 10 min exposure to saturated DMMP vapors. FIG. 10C shows the fluorescence intensity change at 570 nm ($I/I_0$) vs. exposure time (T) under (i) air and (ii) 10 min exposure to saturated DMMP vapors. The source-drain current $I_{ds}$ increased with more negative gate voltages saturating at ~5 V $V_g$, indicating a p-type behavior, although the outputs do not resemble a standard field effect transistor due to the contribution of the metallic SWCNTs. A negative shift of threshold voltage and a decrease in transconductance was observed with exposure to saturated DMMP vapor. Such behaviors have been found in other SWCNT devices, and the shift of threshold voltage and the decrease in transconductance have been respectively attributed to a charge transfer process associated with the analyte and introduction of scattering sites. Another possible source of the resistance changes is that DMMP changes the nature of the Schottky barrier of HFIP-PT/SWCNT-Au contact, however, this cause was less plausible as was determined by passivating the electrode interfaces. Similar results to DMMP were observed when the electrodes interfaces were coated with a 50 um thick film polymethylmethacrylate (PMMA). The effectiveness of PMMA to block the diffusion of DMMP to the sensor was demonstrated by passivating the entire device and under these conditions no response was observed with exposure to DMMP for 60 s.

The presence of the HFIP group was intended to promote strong interactions between the DMMP and HFIP-PT. To probe this interaction, the changes in the fluorescence intensity in response to DMMP were monitored. HFIP-PT is an emissive polymer with a quantum yield of 28% in THF and absorption and emission maxima of 435 and 546 nm, respectively. The dispersions with SWCNTs have a quenched HFIP-PT fluorescence with a decreased quantum yield (corrected for the optical absorptions of the SWCNTs) of 11%.

Spin coated films containing only HFIP-PT prepared in the same fashion as the sensory devices display absorption and emission maxima at 447 and 570 nm, respectively. From comparative studies with thin films of HFIP-PT/SWCNTs, approximately 60% of the emission was quenched by the SWCNTs, thereby indicating that most of the polymer was closely associated with the SWCNTs. The thin film of HFIP-PT exhibited some self-quenching due to interchain interactions and the extended conformation of the PT, and extended exposure to DMMP increased this emission at 570 nm by 55%. In the case of HFIP-PT/SWCNT films (FIG. 10B), the emission at 570 nm was very constant under a flow of air without DMMP, showing this polymer was significantly stable against photo bleaching. Upon exposure to DMMP vapor, the fluorescence was enhanced by 76%. This increase indicates that the polymer bound to the SWCNT was still capable interacting with the DMMP and that quenching by the SWCNT was attenuated. These observations are consistent with DMMP induced conformational changes of the polymer backbone. Therefore, the sensory mechanism may be considered a combination of charge transfer, introduction of scattering sites, and an increased physical separation of the SWCNTs caused by the interaction of the HFIP-PT and DMMP.

Example 2

This example reports the analysis of polymer/CNT sensor in which various binding sites were incorporated within a device.

Figure 12A:
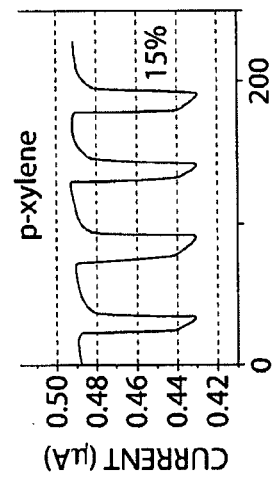
FIG. 12 shows the response signal of a device comprising polymer P3HT and a calixarene binding site, upon exposure to (A) p-xylene, (B) o-xylene, and (C) m-xylene, and the response signal of a device comprising polymer P3HT in the absence of a calixarene binding site, upon exposure to (D) p-xylene, (E) o-xylene, and (F) m-xylene.
FIG. 12G shows the calixarene binding site included in the sensor material of the device employed in FIGS. 12A-12C.
FIG. 12H shows the chemical structure of polymer P3HT.
Figure 12B:
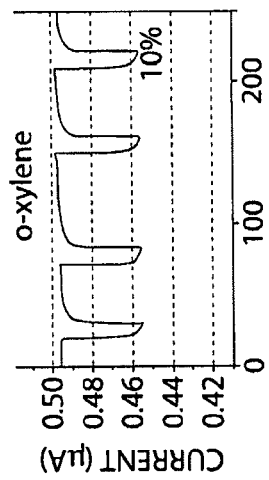
Figure 12C:
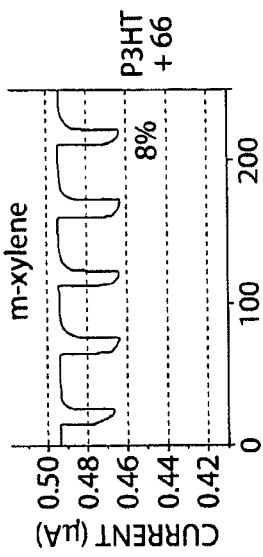
Figure 12D:
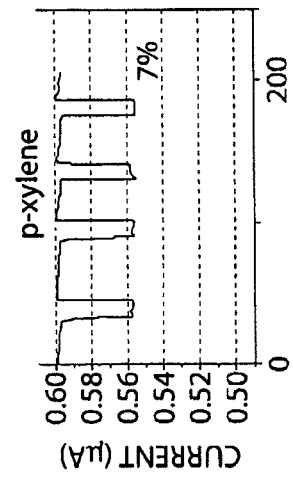
Figure 12E:
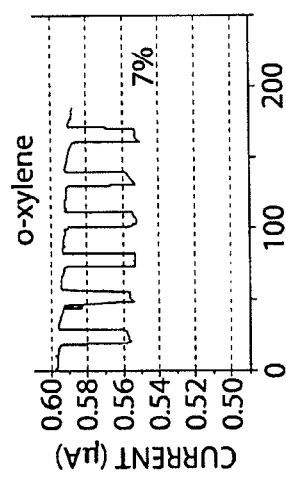
Figure 12F:
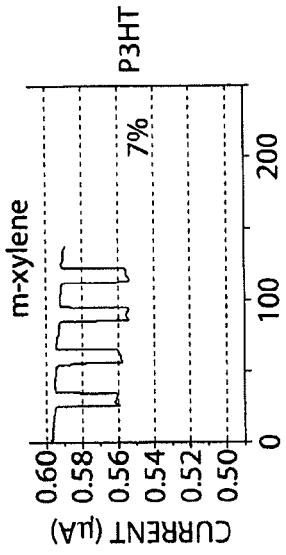
Figure 12G:
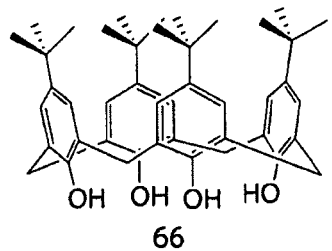
Figure 12H:
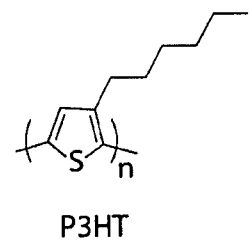
Figure 13:
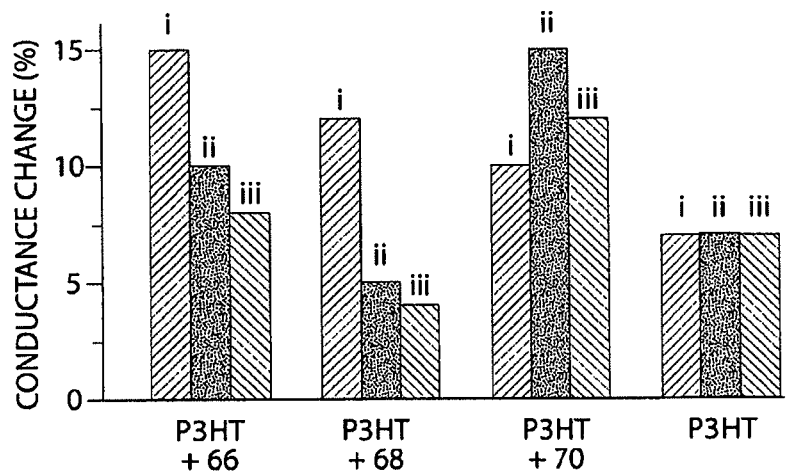
FIG. 13 shows a plot of the conductance change for various devices of the invention upon exposure to (i) p-xylene, (ii) o-xylene, and (iii) m-xylene, wherein the sensor material of the device comprises various calixarene binding sites.
Figure 14A:
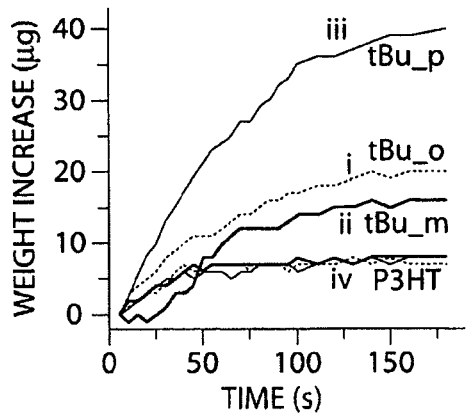
FIG. 14A shows graphs of the weight increase of the sensor material versus time upon exposure to (i) o-xylene, (ii) m-xylene, and (iii) p-xylene, wherein the sensor material of the device comprises a calixarene binding site, and (iv) the weight increase of the sensor material versus time of the sensor material which does not comprise a calixarene binding site.
Figure 14B:
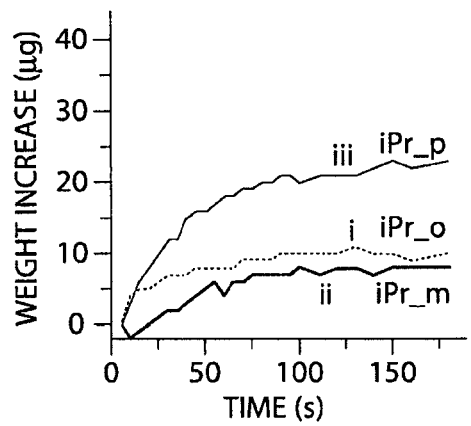
FIGS. 14B-14C show graphs of the weight increase of the sensor material versus time upon exposure to (i) o-xylene, (ii) m-xylene, and (iii) p-xylene, wherein the sensor material of the device comprises calixarene binding sites.
Figure 14C:
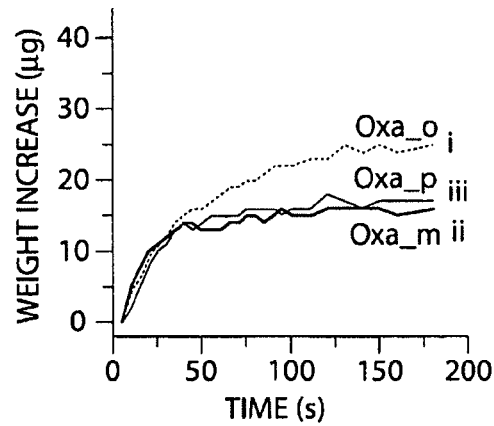

To detect xylene isomers, a series of calixarenes of different conformation were mixed with P3HT and SWCNTs. The device was fabricated in a similar fashion as Example 1, with the binding site (e.g., a calixarene) being mixed with the polymer. FIG. 11A shows the three isomers of xylene, ortho-xylene 60, meta-xylene 62 and para-xylene 64. FIG. 11B shows the calixarenes that were investigated in this example, p-tert-butylcalix[4]arene (66), p-isopropylcalix[4]arene (68), and p-isopropyldihomooxa-calix[4]arene (70). The sensors were exposed to 400 ppm of xylenes. FIG. 12 shows the response of the sensors containing calixarene 66 shown in FIG. 12G when exposed to 400 ppm of xylene. FIGS. 12A, 12B, and 12C show the response of P3HT containing calixarene 66 to xylene isomers 64, 62 and 60, respectively. FIG. 12H shows the structure of P3HT. FIGS. 12D, 12E, and 12F show the response of P3HT containing no added binding sites to xylene isomers 64, 62 and 60 respectively. FIG. 13 shows a plot of the conductance change versus the calixarene added to P3HT. Sensors with a calixarene added to P3HT gave different responses to the isomers of xylene while the sensor that contained no additive gave the same response for all isomers of xylene. FIG. 14A shows a graph of the weight increase (ug) of the sensor material which comprises calixarene 66 when exposed to (i) o-xylene, (ii) m-xylene and (iii) p-xylene, and (iv) the weight increase of the sensor material which does not comprise a binding site. FIGS. 14B-C show plots of the weight increase (ug) of the sensor material which comprises binding site 68 and 70, respectively, when exposed to (i) o-xylene, (ii) m-xylene and (iii) p-xylene.

Example 3

This example reports the analysis of polymer/CNT sensors in which a binding site has been added, specifically a palladium complex.

Figure 15B:
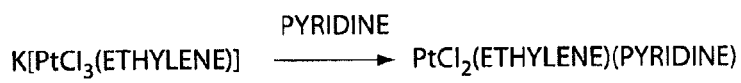
FIG. 15B shows the synthesis of $Pt(Cl_2)$(ethylene)(pyridine), according to one embodiment of the invention.
Figure 16A:
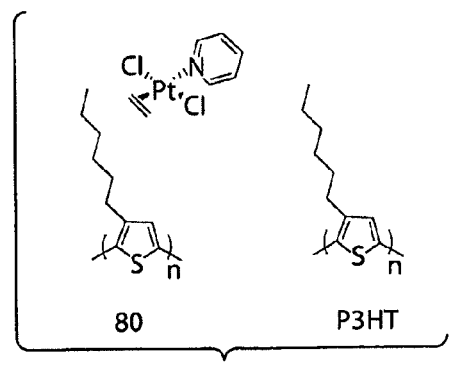
FIG. 16A shows chemical structures of polymer materials, including a polymer material comprising a binding site, according to some embodiments of the invention.
Figure 16B:
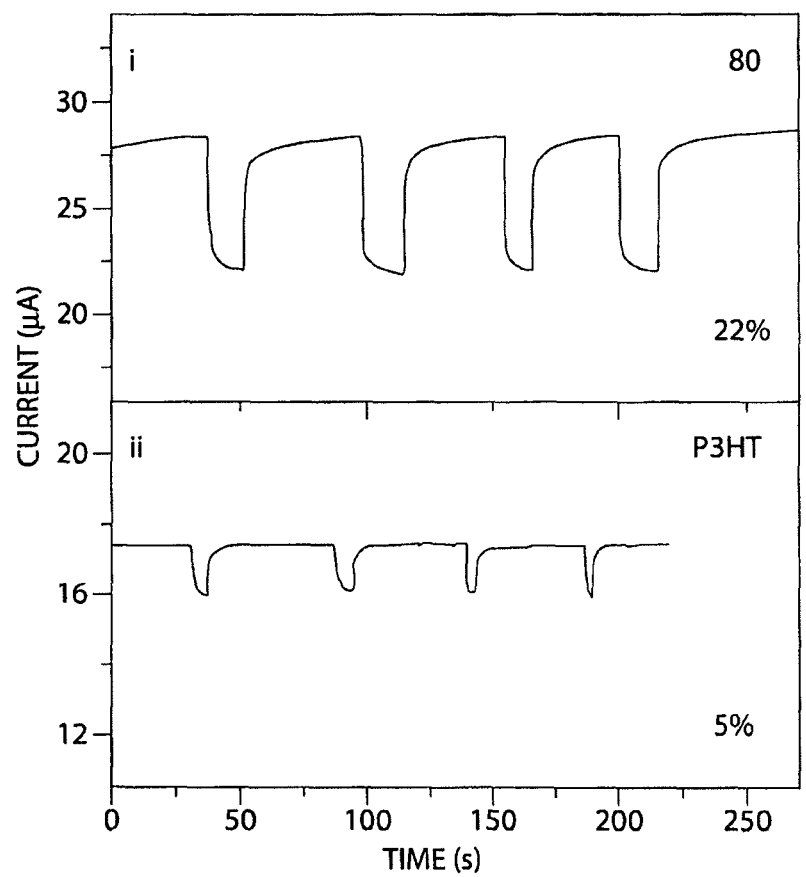
FIG. 16B shows the change in current versus time of devices upon exposure to an analyte, wherein the device comprises (i) a sensor material comprising a binding site, and (ii) a sensor material that does not comprise a binding site.

Binding sites for olefins were integrated into a sensor to improve the sensitivity of the sensor for olefin analytes. One such type of binding site that may be added to a sensor to increase selectivity for olefins is $PtCl_2$(olefin)(pyridine). An example of how $PtCl_2$(olefin)(pyridine) may associated with an olefin is depicted in FIG. 15A. As shown in FIG. 15B, $PtCl_2$(ethylene)(pyridine) may be synthesized by reaction of $K[PtCl_3$(ethylene)] and pyridine. The device was fabricated in a similar fashion as Example 1, with the binding site ($PtCl_2$(olefin)(pyridine)) being mixed with the polymer. FIG. 16A shows P3HT which was compared with P3HT containing the binding site (80). FIG. 16B shows the response of P3HT and 80 to an atmosphere of saturated hexene. The sensor containing P3HT (and no binding site) exhibits a response of 5% while the sensor containing 80 exhibits are response of 22%.

Figure 16C:
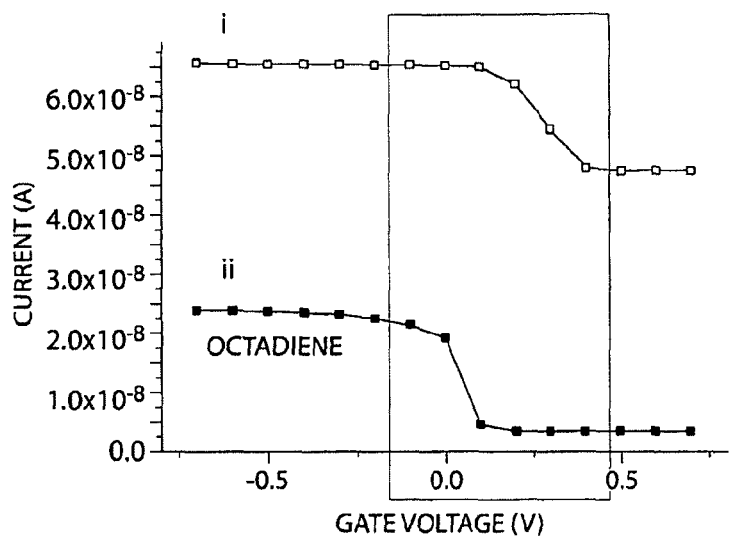
FIG. 16C shows a graph of the source-drain current versus gate voltage of the device under conditions of (i) air, and (ii) saturated octadiene vapor.

FIG. 16C shows a graph of the source-drain current versus gate voltage of the device under conditions of (i) air and (ii) saturated octadiene vapor. The source-drain bias voltage is fixed at 50 mV. The gate voltage was scanned from 0.8 V to −0.8 V. As shown in FIG. 16C, the source-drain current increased with more negative gate voltages saturating at ~0.15 V $V_g$, indicating a p-type behavior; and the small on-off ratio is due to the contribution of metallic SWCNTs. A negative shift of threshold voltage and a decrease in transconductance with exposure to saturated octadiene vapor were also observed. Without wishing to be bound by theory, the shift of threshold voltage and the decrease in transconductance may be respectively attributed to a charge transfer process associated with the analyte and introduction of scattering sites within the device.

Example 4

Figure 17:
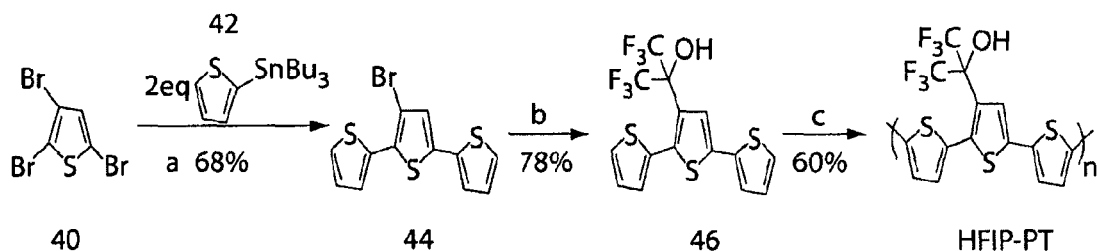
FIG. 17 shows the synthesis of polymer HFIP-PT, according to one embodiment of the invention.

Poly(3'-Hexafluoroisopropanol-2,2':5',2''-terthiophene) (HFIP-PT) was synthesized as follows. HFIP-PT was synthesized via oxidative polymerization (FIG. 17). Stille-type cross-coupling reaction between stannylated 42 and tribromothiophene 40 afforded bromoterthiophene 44, which was transformed to HFIP-substituted terthiophene 46 via lithiation and hexafluoroacetone quenching. Oxidizing of monomer 3 by iron chloride gave rise to HFIP-PT.

Example 5

Synthesis of S-1.1 3'-bromo-2,2':5',2''-terthiophene (44) proceeded as follows. In a 100 mL round-bottom flask were added 2,3,5-tribromothiophene (1.4 mL, 11 mmol), 2-(tributylstannyl)thiophene (7 mL, 22 mmol), tetrakis(triphenylphosphine)palladium(0) and dimethylformamide (30 mL). The mixture was stirred at 80° C. for 24 h under nitrogen atmosphere. It was then diluted with ether (100 mL), washed with HCl and then brine, dried over $MgSO_4$, and evaporated under reduced pressure. The resulting crude product was purified by column chromatography (hexane), providing 2.46 g of a light yellow, viscous oil (yield 68%). $^1H$ NMR (300 MHz, $CDCl_3$) δ: 7.43 (dd, 1H, J=1.2, 3.6 Hz), 7.36 (dd, 1H, J=1.2, 5.1 Hz), 7.27 (dd, 1H, J=1.2, 5.1 Hz), 7.19 (dd, 1H, J=1.2, 3.6 Hz), 7.09 (dd, 1H, J=3.6, 5.1 Hz), 7.08 (s), 7.04 (dd, 1H, J=3.6, 5.1 Hz). $^{13}C$ NMR (75 MHz, $CDCl_3$) δ: 135.7, 135.6, 134.1, 130.7, 128.0, 127.6, 127.2, 126.5, 126.1, 125.3, 124.3, 107.8. IR (KBr) v/cm$^{-1}$: 3105, 3080, 1664, 1493, 1420, 1223, 1048, 848, 815, 710.

Example 6

Synthesis of S-1.2 3'-hexafluoroisopropanol-2,2':5',2''-terthiophene (46) proceeded as follows. Into a 100 mL round-bottom flask was added 0.327 g (1.0 mmol) of 2 and 10 mL of hexane under nitrogen atmosphere. The mixture was cooled to −78° C., and 0.75 mL of a 1.6 M solution (1.2 mmol) of n-butyllithium in hexanes was added slowly by syringe. After the addition was complete, 1 mL of tetrahydrofuran was added to give a homogenous mixture. After 0.5 h, 2 mL of more hexane was added and the solution was allowed to warm to 0° C. for 30 min. The addition funnel was quickly replaced with a Dewar-type condenser under a heavy flow of argon. The condenser was charged with dry ice and acetone and an excess of anhydrous gaseous hexafluoroacetone was then condensed into the flask. The reaction mixture was allowed to warm to room temperature, and the hexafluoroacetone was allowed to reflux at RT for 3 h. Excess hexafluoroacetone was removed by flushing the apparatus with argon for several hours. A bubbler filled with 10% aqueous NaOH solution was used to trap the reactive vapor. The reaction mixture was treated with a 5% HCl solution (25 mL) and extracted with diethyl ether (200 mL). The organic extracts were washed with water (100 mL×2) and brine (100 mL) and dried over MgSO$_4$. The residue was purified by column chromatography (8% ethyl acetate in hexanes) to yield 0.20 g (48.3%) of a crystalline solid; mp 85-86° C. $^1$H NMR (300 MHz, CDCl$_3$) δ: 7.42 (dd, 1H, J=1.2, 3.6 Hz), 7.33 (m, 2H), 7.18 (dd, 1H, J=1.2, 5.1 Hz), 7.08 (s, 1H), 6.99 (dd, 1H, J=3.6, 5.1 Hz), 6.94 (dd, 1H, J=3.6, 5.1 Hz), 3.86 (s, 1H). $^{13}$C NMR (75 MHz, CDCl$_3$) δ: 139.00, 135.43, 134.38, 131.30, 130.13, 128.15, 127.82, 126.95, 126.03, 125.19, 123.21, 123.14. $^{19}$F NMR (282 MHz, CDCl$_3$) δ: −76.41. FT-IR (KBr) v/cm$^{−1}$: 3473, 3092, 2921, 1804, 1628, 1570, 1540, 1507, 1467, 1428, 1415, 1359, 1260, 1238, 1219, 1158, 1118, 1045, 1006, 956, 886, 836, 797, 712. HRMS (EI): calcd for C$_{15}$H$_8$F$_6$OS$_3$ (M$^+$), 413.9636, found 413.9638.

Example 7

Synthesis of S-1.3 poly(3'-hexafluoroisopropanol-2,2':5', 2"-terthiophene) (HFIP-PT) proceeded as follows. To a 25 mL round-bottom flask with anhydrous iron trichloride (20 mg, 0.4 mmol) in chloroform (15 mL) was added 3 (41 mg, 0.1 mmol) in a chloroform solution (0.5 mL). The mixture was sonicated for 2 h, and then stirred at room temperature for 24 h. It was then diluted with tetrahydrofuran (100 mL), reduced with sodium thiosulphate (0.5 g), then washed sequentially with water (100 mL), 0.1 M hydrazine aqueous solution (100 mL), water (100 mL), brine (100 mL), dried over MgSO$_4$, filtered with a 0.2 um PTFE filter and evaporated to 10 mL under reduced pressure. The polymer solution was then precipitated into 30 mL of hexane. The precipitate was isolated by centrifugation and decantation of the liquid. The precipitate was dissolved in tetrahydrofuran (5 mL) and precipitated into hexane again. The precipitation was repeated once more. The material was dried under vacuum to yield a orange-red solid (20 mg, 50%). According to gel-permeation chromatography (polystyrene standards), HFIP-PT has an Mn=25.3K and a polydispersity index (PDI)=2.3. $^1$H NMR (300 MHz, CDCl$_3$) δ: 7.26 (aromatic C—H), 7.19 (aromatic C—H), 7.15 (aromatic C—H), 3.97 (O—H). $^{19}$F NMR (282 MHz, CDCl$_3$) δ: −76.24. FT-IR (KBr) v/cm$^{−1}$: 3451, 2361, 1637, 1468, 1309, 1260, 1224, 1189, 1120, 1102, 1075, 960, 794, 740, 726.

Example 8

The following example describes the photophysical analysis of HFIP-PT.

FIG. 18 shows the UV-vis absorption and fluorescence emission spectra of polymer HFIP-PT in chloroform solution (solid lines) and as thin films (dotted lines). The thin-film spectra from polymer HFIP-PT show a broadened absorption (from 435 nm with an extinction coefficient of 1.96×10$^4$ M$^{−1}$ cm$^{−1}$ per repeating unit in solution to 447 nm in film) and emission (from 546 nm in solution to 570 nm in the thin film). The shifts to longer wavelength are typical of conjugated polymers and likely represent a combination of aggregation and planarization of the polymer backbones.

Example 9

The following example describes the formation of a dispersion of single-walled carbon nanotubes in HFIP-PT.

Single-wall carbon nanotubes were dispersed in HFIP-PT solution by sonication. FIG. 19 shows photographs of (A) a polymer solution and HFIP-PT/SWCNT solutions ((B) SWCNT~0.05 mg/mL; (C) SWCNT~1 mg/mL) in THF. A transparent solution of HFIP-PT/SWCNT system was observed, which remains stable for at least one year. Since the HFIP-PT/SWCNT system is very soluble, traditional polymer-processing methods, such as spin-coating and ink-jet printing may be utilized to fabricate transistors, LEDs and other devices. The experiment was conducted by mixing purified SWCNT (5 mg) and HFIP-PT (5 mg) in 5 mL tetrahydrofuran followed by ultrasonication for 2 hours. This HFIP-PT/SWCNT mixture was purified by high speed centrifugation (4500 rpm, 60 minutes), to achieve uniform SWCNT dispersion. The upper 80% of supernatant was collected, leaving ~0.3 mg of undissolved SWCNT precipitated.

Example 10

Figure 20B:
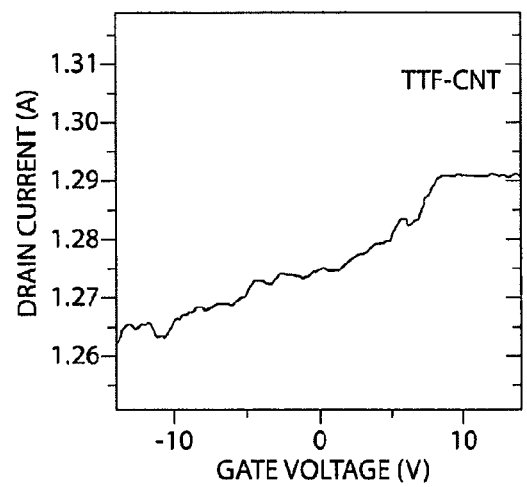
FIG. 20B shows a graph of the drain current as a function of voltage for a device comprising a polymer material and TTF binding sites according to one embodiment of the invention.
Figure 20C:
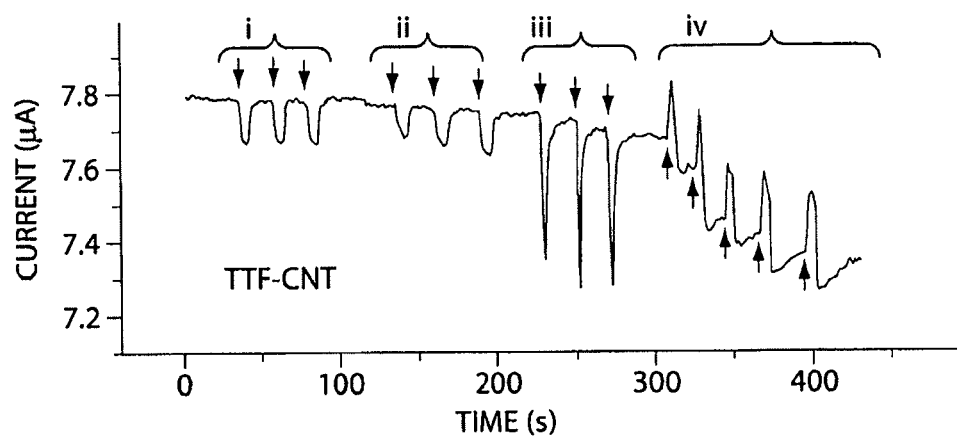
FIG. 20C shows the response signal of a device comprising a sensor material (e.g., polymer P3HT) upon exposure to (i) DNT, (ii) DNB, (iii) toluene, and (iv) DMMP, wherein the sensor material comprises TTF binding sites.
Figure 20D:
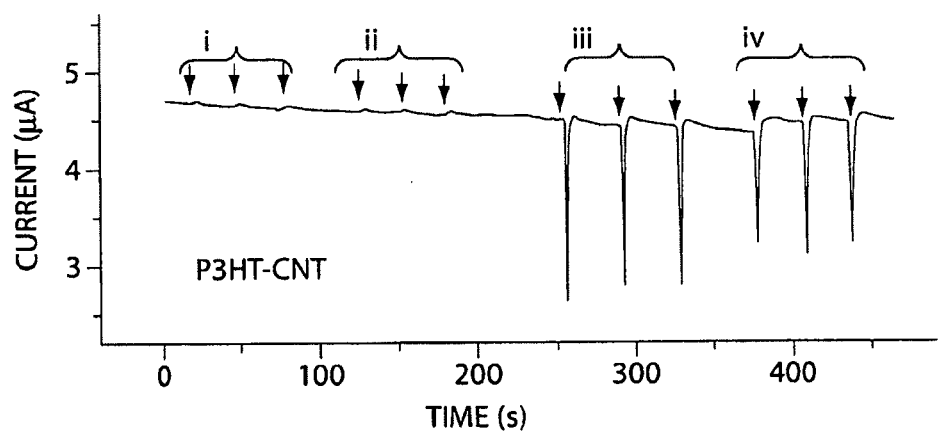
FIG. 20D show the response signals of a device comprising a sensor material (e.g., polymer P3HT) upon exposure to (i) DNT, (ii) DNB, (iii) toluene, and (iv) DMMP, wherein the sensor material does not comprise TTF binding sites.

The following example describes the use of devices including additional components capable of pi-stacking with carbon nanotubes, in the determination of nitroaromatic molecules. Addition of a binding site such as tetrathiafulvalene (TTF) compounds to a polymer/CNT sensor may allow the transduction mechanism of the sensor to include charge transfer interactions. Tetrathiafulvalene compounds may be capable of pi-stacking with the carbon nanotubes, and, therefore, may be capable of doping the sensor material via charge-transfer. One embodiment of the synthesis of a tetrathiafulvalene compound (TTF) is shown in FIG. 20A. The device was fabricated using methods as described in Example 1, with the binding site TTF being mixed with the polymer. FIG. 20B shows a graph of drain current versus voltage of the device comprising a polymer material and TTF binding sites. FIG. 20C shows the response signal of a device comprising a sensor material (e.g., polymer P3HT) upon exposure to (i) DNT, (ii) DNB, (iii) toluene and (iv) DMMP, wherein the sensor material comprises TTF binding sites. FIG. 20D show the response signals of a device comprising a sensor material (e.g., polymer P3HT) upon exposure to (i) DNT, (ii) DNB, (iii) toluene and (iv) DMMP, wherein the sensor material does not comprise TTF binding sites.

Example 11

The following example describes the use of devices including covalently functionalized SWCNTs in the determination of various analytes.

Figure 21A:
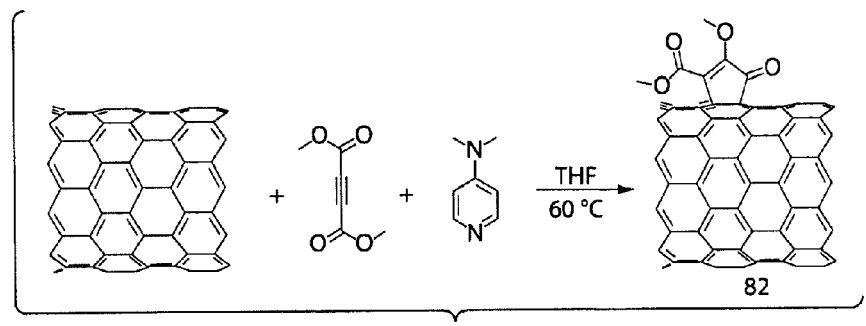
FIGS. 21A-C show the synthesis of functionalized carbon nanotubes, according to some embodiments of the invention.
Figure 21B:
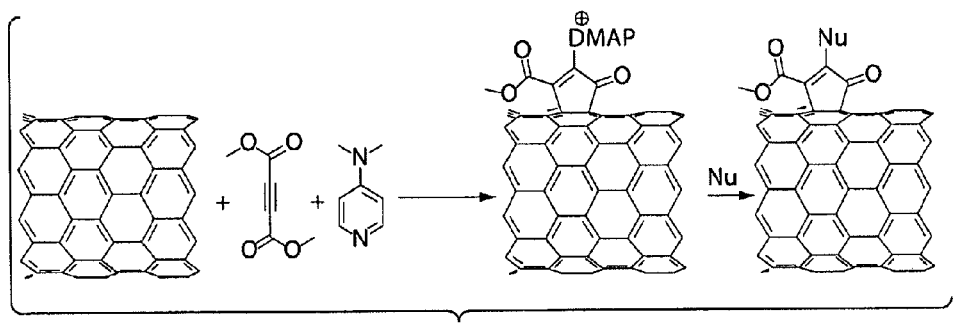
Figure 21C:
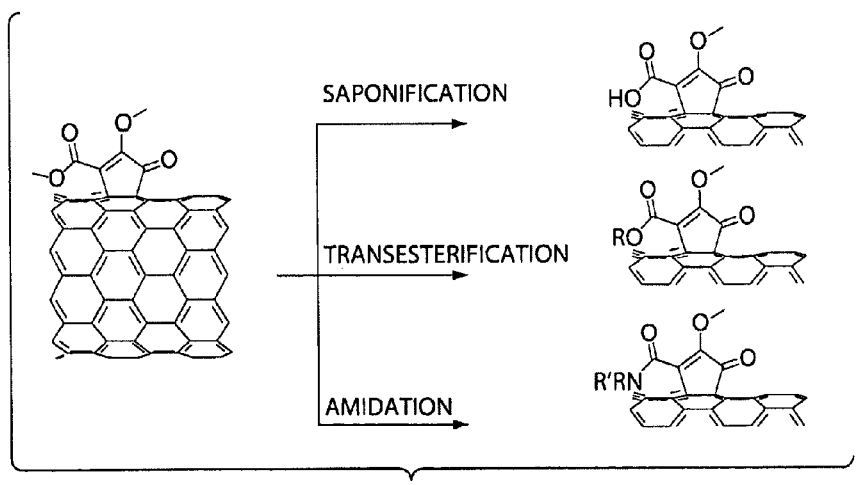
Figure 21D:
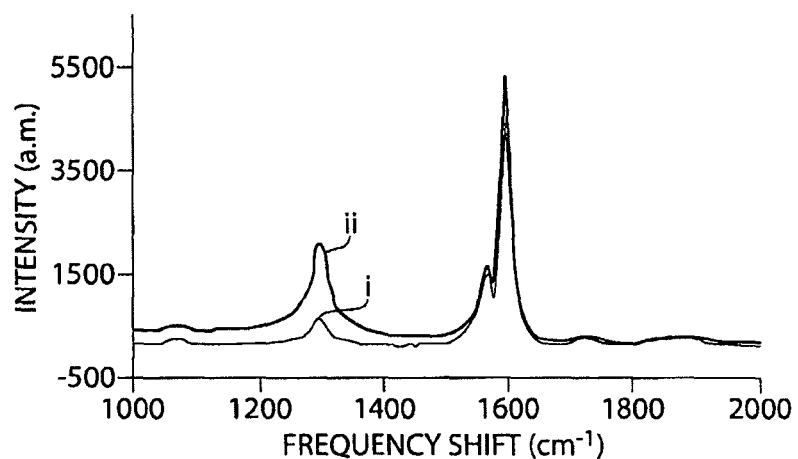
FIG. 21D shows Raman spectra of an (i) unfunctionalized, and (ii) functionalized SWCNTs.

FIGS. 21A-21C show the synthesis of various covalently functionalized SWCNTs. The Raman spectra of an (i) unfunctionalized and (ii) functionalized SWCNTs are shown in FIG. 21D. As observed in this FIG. 21D, functionalization of the SWCNT may lead to an increase in the D-band (e.g. the disorder mode) and therefore, a significant amount of sp$^2$ carbon hybridization may become sp$^a$ carbon hybridization.

Figure 21E:
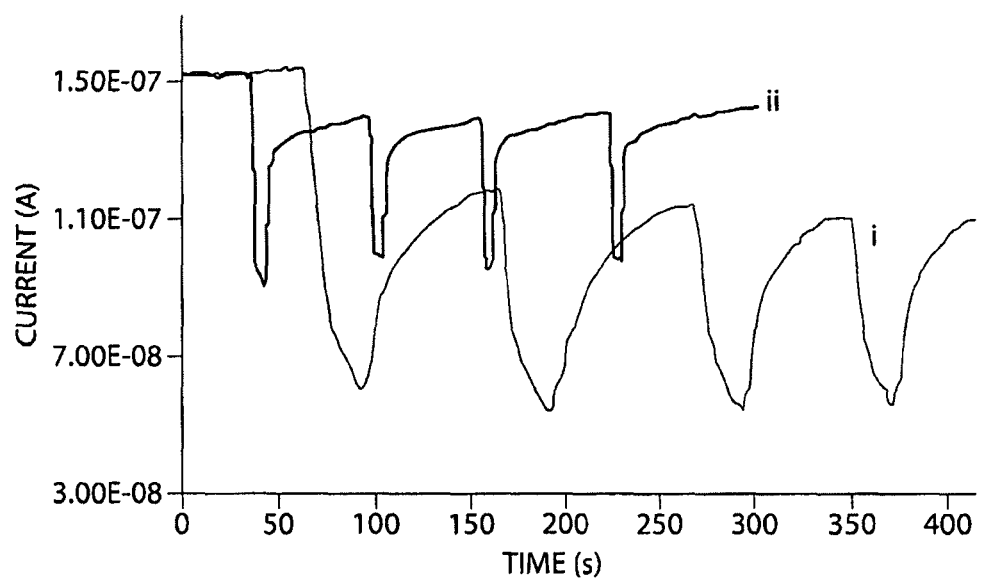
FIG. 21E shows the response signals of a device comprising functionalized single-walled carbon nanotubes (SWCNTs) upon exposure to an atmosphere of (i) DMHP, and (ii) THF.

A device was fabricated in a similar fashion as Example 1, wherein the carbon nanotubes 82 employed were functionalized as shown FIG. 21A. FIG. 21E shows the response of the device upon exposure to an atmosphere of (i) DMHP and (ii) THF. The device may be regenerated by flowing hot air (e.g. 70° C.) on the device (e.g., sensor material).

Example 12

The following example describes the use of devices including covalently functionalized MWCNTs in the determination of various analytes.

Figure 22A:
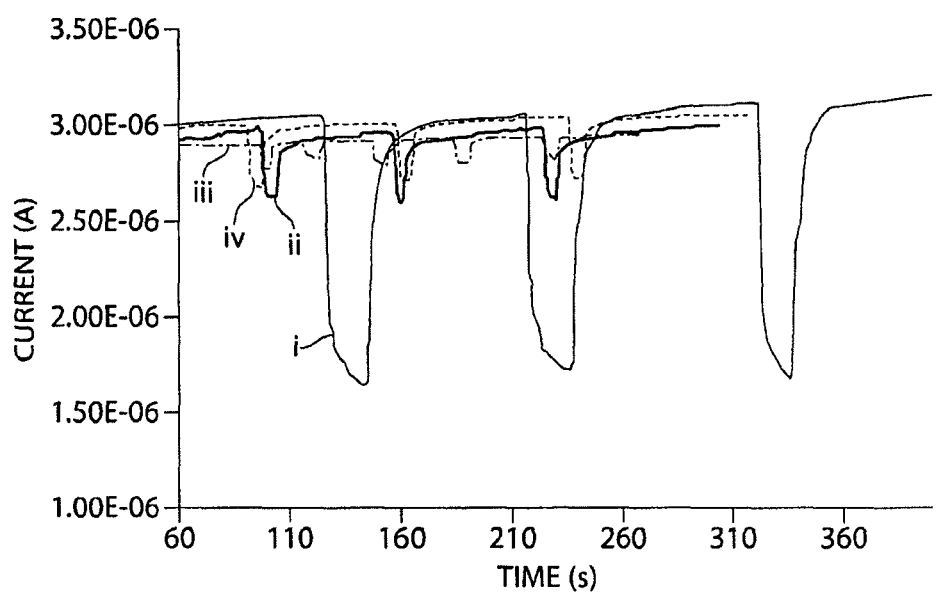
FIG. 22A shows the response signal of a device comprising functionalized multi-walled carbon nanotubes (MWCNTs) upon exposure to an atmosphere of (i) DMHP, (ii) THF, (iii) toluene, and (iv) nitrobenzene.
Figure 22B:
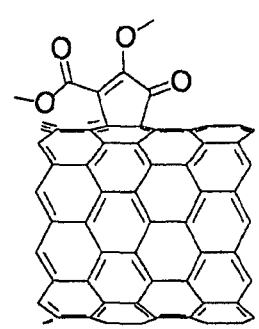
FIG. 22B shows the structure of a functionalized MWCNT, according to one embodiment of the invention.

MWCNTs were functionalized according to the synthetic procedures as outlined above in Example 11. A device was fabricated in a similar fashion as Example 1, wherein functionalized MWCNTs were employed. The functionalized MWCNTs employed in this example were MWCNTs 91 as shown in FIG. 22B. FIG. 22A shows the response of the device upon exposure to an atmosphere of (i) DMHP, (ii) THF, (iii) toluene, and (iv) nitrobenzene. As determined from the response of the device, functionalized MWCNTs 91 show a higher response towards, quicker release of, and greater selectivity towards analytes comprising a phosphate group, as compare to analytes that do not comprise a phosphate group. In this case, the low response of the device to THF, toluene, and nitrobenzene may be attributed to trapping of the analytes between the unfunctionalized inner carbon nanotubes and the functionalized outer carbon nanotubes.

Example 13

The following example describes the use of devices including covalently functionalized MWCNTs in the determination of various analytes.

Figure 23A:
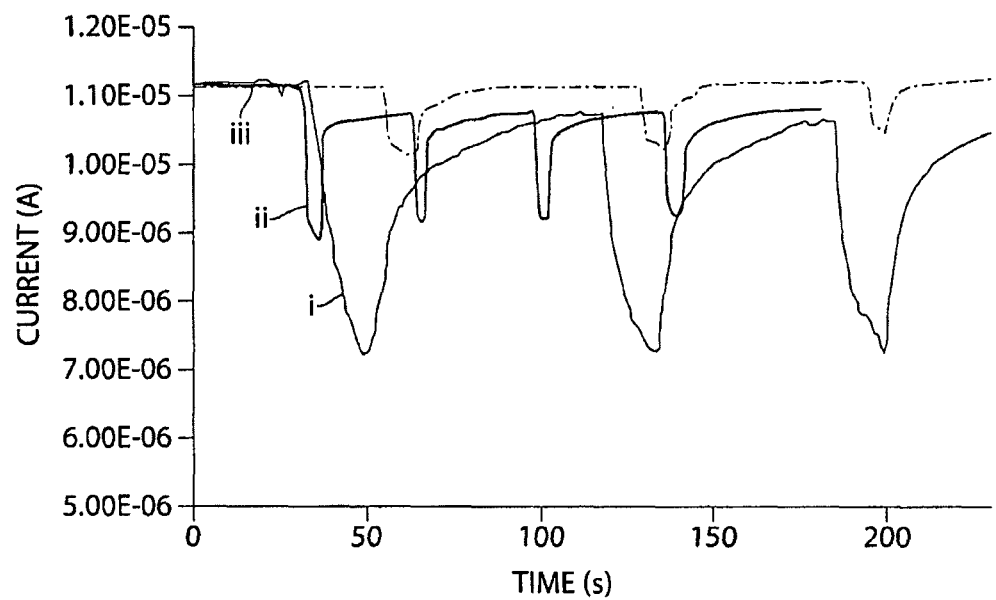
FIG. 23 shows (A) the response signals of a device comprising functionalized MWCNTs upon exposure to an atmosphere of (i) DMHP, (ii) THF, (iii) toluene, and (B) the structure of a functionalized MWCNT, according to one embodiment of the invention.
Figure 23B:
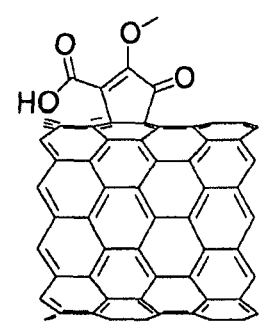

MWCNTs were functionalized according to the synthetic procedures as outlined above in Example 11. A device was fabricated in a similar fashion as Example 1, wherein functionalized MWCNTs were employed. The functionalized MWCNTs employed in this example were MWCNTs 92 as shown in FIG. 23B. FIG. 23A shows the response of the device upon exposure to an atmosphere of (i) DMHP, (ii) THF, and (iii) toluene. As determined from the response of the device, functionalized MWCNTs 92 show a higher response towards, quicker release of, and greater selectivity towards analytes comprising a phosphate group, as compare to analytes that do not comprise a phosphate group.

Example 14

The following example describes the use of devices including covalently functionalized MWCNTs in the determination of various analytes.

Figure 24A:
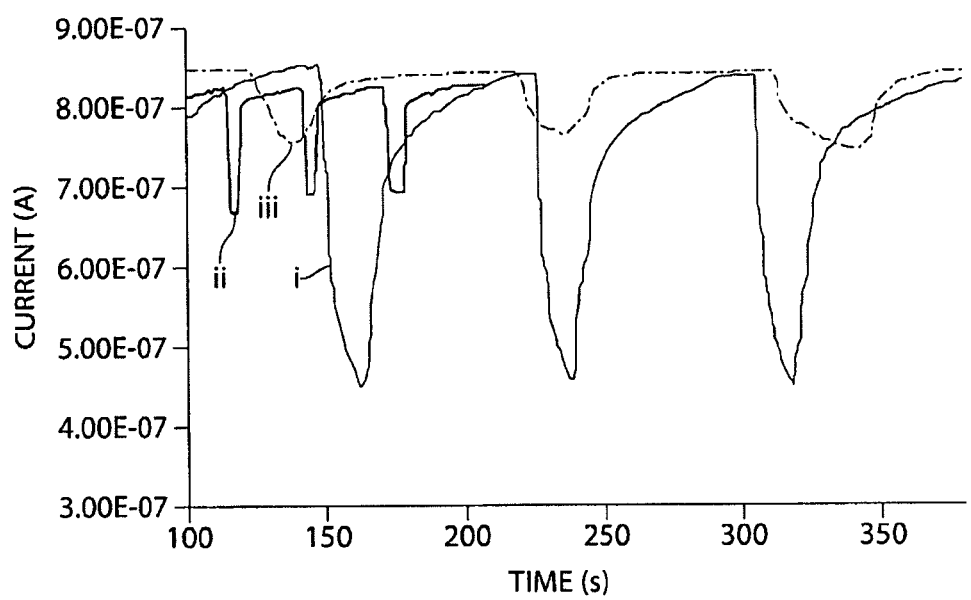
FIG. 24 shows (A) the response signals of a device comprising functionalized MWCNTs upon exposure to an atmosphere of (i) DMMP, (ii) THF, (iii) toluene, and (B) the structure of a functionalized MWCNT, according to one embodiment of the invention.
Figure 24B:
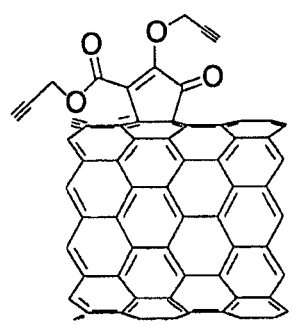

MWCNTs were functionalized according to the synthetic procedures as outlined above in Example 11. A device was fabricated in a similar fashion as Example 1, wherein functionalized MWCNTs were employed. The functionalized MWCNTs employed in this example were MWCNTs 93 as shown in FIG. 24B. FIG. 24A shows the response of the device upon exposure to an atmosphere of (i) DMMP, (ii) THF, and (iii) toluene. As determined from the response of the device, functionalized MWCNTs 93 show a higher response towards, quicker release of, and greater selectivity towards analytes comprising a phosphate group, as compare to analytes that do not comprise a phosphate group. The slower release rate of DMHP versus DMMP may be due to hydrogen-bonding between DMHP and the triazole group of functionalized MWCNTs 93.

Example 15

The following example describes the use of devices including covalently functionalized MWCNTs in the determination of various analytes.

Figure 25A:
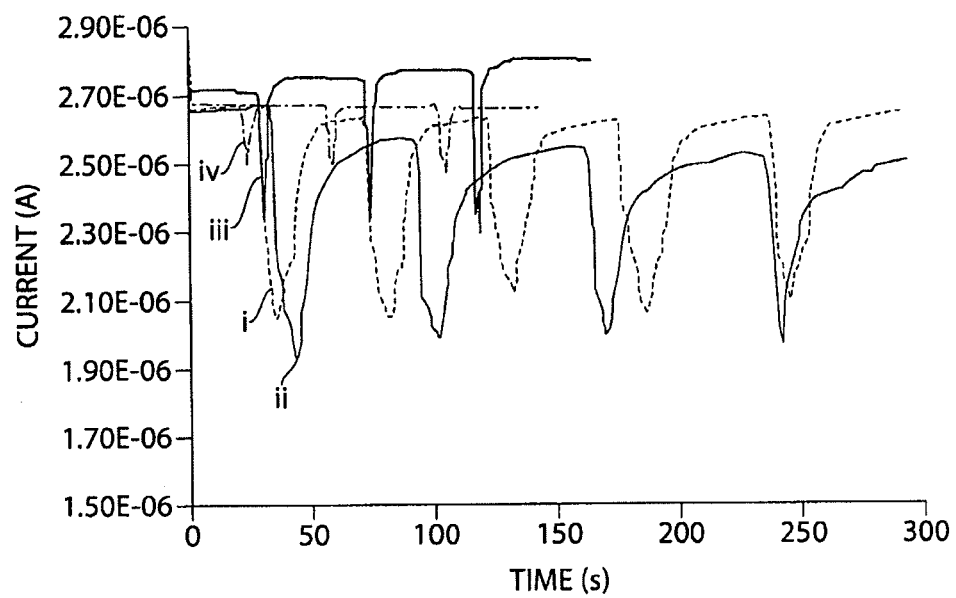
FIG. 25 shows (A) the response signals of a device comprising functionalized MWCNTs upon exposure to an atmosphere of (i) DMMP, (ii) DMHP, (iii) THF, and (iv) toluene, and (B) the structure of a functionalized MWCNT, according to one embodiment of the invention.
Figure 25B:
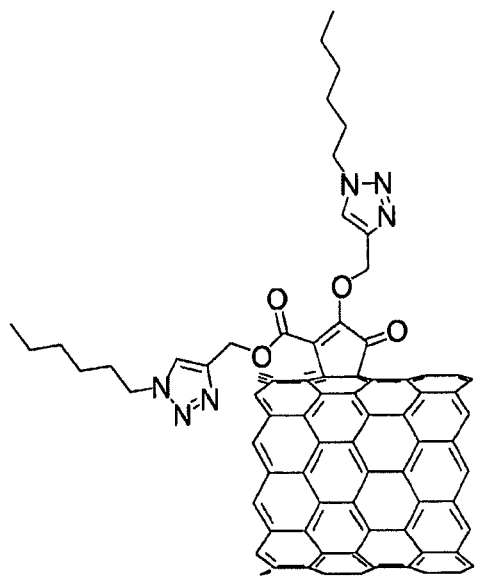

MWCNTs were functionalized according to the synthetic procedures as outlined above in Example 11. A device was fabricated in a similar fashion as Example 1, wherein functionalized MWCNTs were employed. The functionalized MWCNTs employed in this example were MWCNTs 94 as shown in FIG. 25B. FIG. 25A shows the response of the device upon exposure to an atmosphere of (i) DMMP, (ii) DMHP, (iii) THF, and (iv) toluene. As determined from the response of the device, functionalized MWCNTs 94 show a higher response towards, quicker release of, and greater selectivity towards analytes comprising a phosphate group, as compare to analytes that do not comprise a phosphate group. The slower release rate of DMHP versus DMMP may be due to hydrogen-bonding between DMHP and the triazole group of functionalized MWCNTs 94.

Example 16

The following example describes the use of devices including covalently functionalized MWCNTs in the determination of various analytes.

Figure 26A:
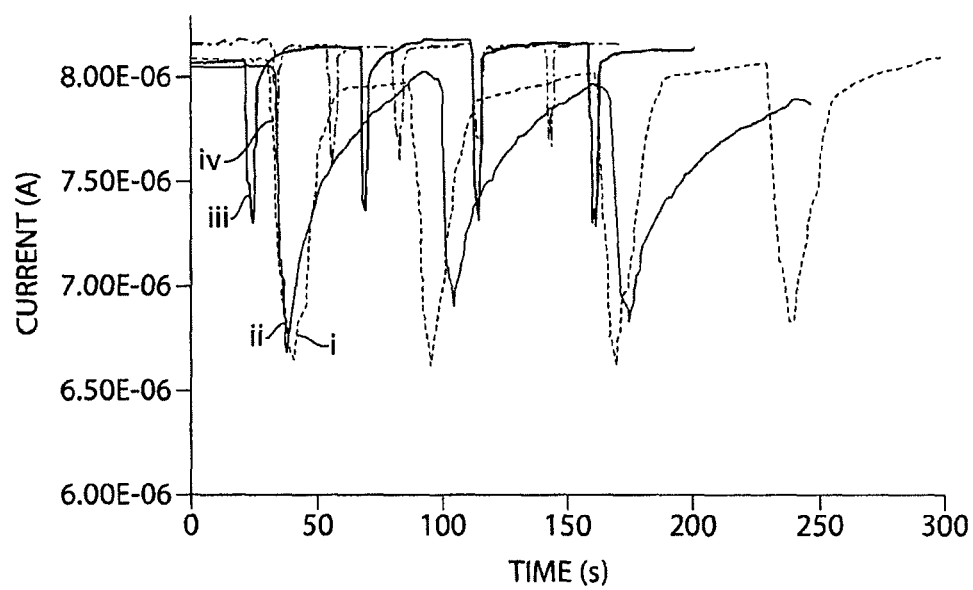
FIG. 26A shows (A) the response signals of a device comprising functionalized MWCNTs upon exposure to an atmosphere of (i) DMMP, (ii) DMHP, (iii) THF, and (iv) toluene, and (B) the structure of a functionalized MWCNT, according to one embodiment of the invention.
Figure 26B:
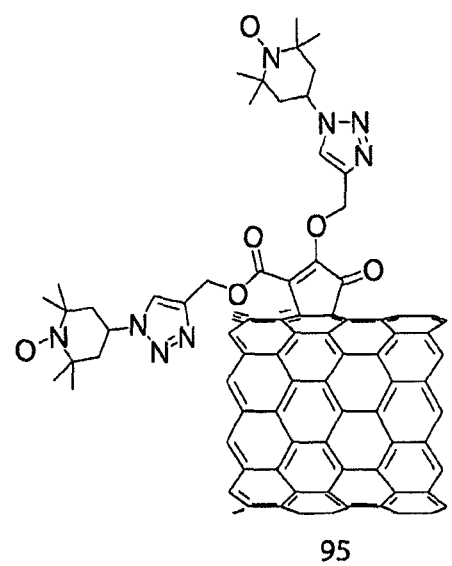

MWCNTs were functionalized according to the synthetic procedures as outlined above in Example 11. A device was fabricated in a similar fashion as Example 1, wherein functionalized MWCNTs were employed. The functionalized MWCNTs employed in this example were MWCNTs 95 as shown in FIG. 26B. FIG. 26A shows the response of the device upon exposure to an atmosphere of (i) DMMP, (ii) DMHP, (iii) THF, and (iv) toluene. As determined from the response of the device, functionalized MWCNTs 95 show a higher response towards, quicker release of, and greater selectivity towards analytes comprising a phosphate group, as compare to analytes that do not comprise a phosphate group. The slower release rate of DMHP versus DMMP may be due to hydrogen-bonding between DMHP and the triazole and/or TEMPO group of functionalized MWCNTs 95.

Example 17

The following example describes the use of devices including covalently functionalized MWCNTs in the determination of various analytes.

Figure 27A:
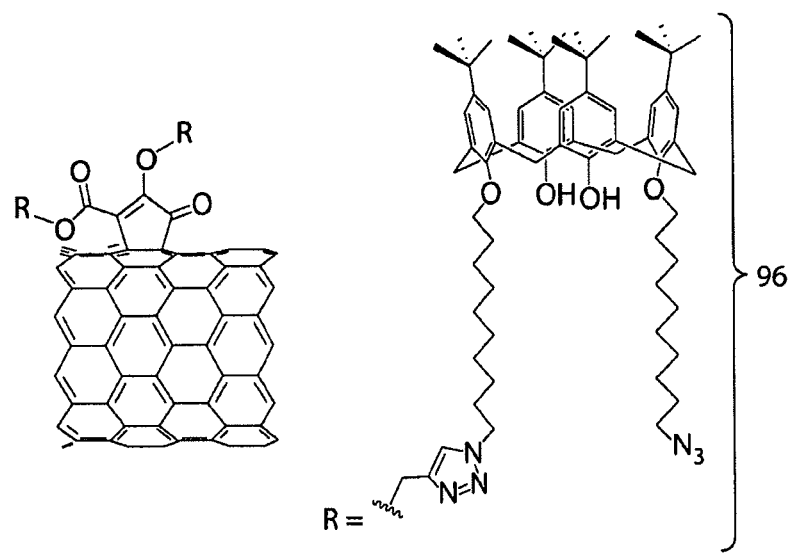
FIG. 27 shows (A) the structure of a functionalized MWCNT, according to one embodiment of the invention, (B) the response signals of a device comprising functionalized MWCNTs upon exposure to an atmosphere of (i) DMHP, (ii) THF, and (iii) toluene, and (C) the response signal of a device upon alternating exposure to (i) nitrobenzene and (ii) toluene.
Figure 27B:
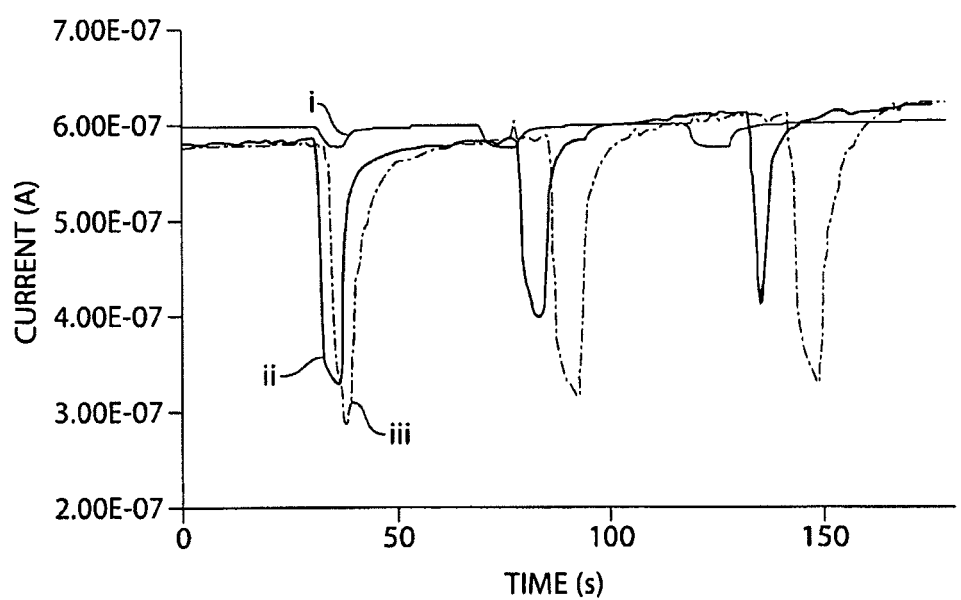
Figure 27C:
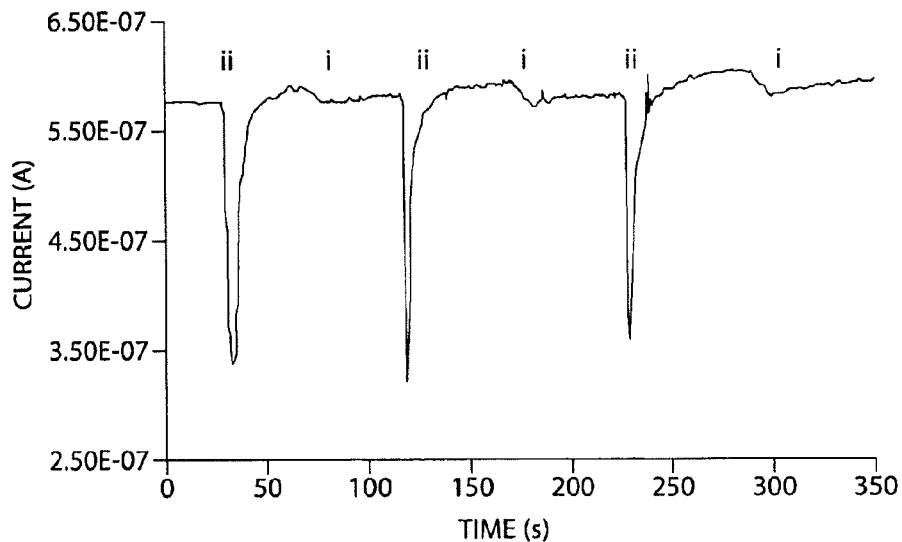

MWCNTs were functionalized according to the synthetic procedures as outlined above in Example 11. A device was fabricated in a similar fashion as Example 1, wherein functionalized MWCNTs were employed. The functionalized MWCNTs employed in this example were MWCNTs 96 as shown in FIG. 27A. FIG. 27B shows the response of the device upon exposure to an atmosphere of (i) DMHP, (ii) THF, and (iii) toluene. As determined from the response of the device, functionalized MWCNTs 96 show a greater response to toluene and THF than to DMHP. This may be due to the MWCNT surface being highly occupied by the calixarene groups which may control the analyte access to the carbon nanotube. Therefore, the size of the analyte (e.g., toluene and THF are smaller than DMHP) may determine the association of the analyte with the sensor material, and hence, the response of the device to these analytes. FIG. 27C shows the response of the same device upon alternating exposure to (i) toluene and (ii) nitrobenzene. The device was observed to be more sensitive to toluene than to nitrobenzene, a result which may be attributed to the electronic nature of the analytes.

Example 18

The following example describes the synthesis and use of functionalized polythiophenes with a number average molecular weight of at least about 70,000. In some cases, repeated analyte exposure, storage for long periods of time, and/or exposure to heat may cause the sensitivity of a sensor to decrease. Without wishing to be bound by theory, this may be due to disassociation of the polymer from the SWCNTs. The disassociation may be reduced by forming dispersions comprising higher molecular weight (Mn>100,000) polythiophenes and SWCNTs. This may be due to enhanced dispersion stability enabled by the higher molecular weight polymer because of increased polymer wrapping around the SWCNTs and may lead to sensory materials with increased stability.

Synthesis of High Molecular Weight HFIP Polymer.

Figure 28:
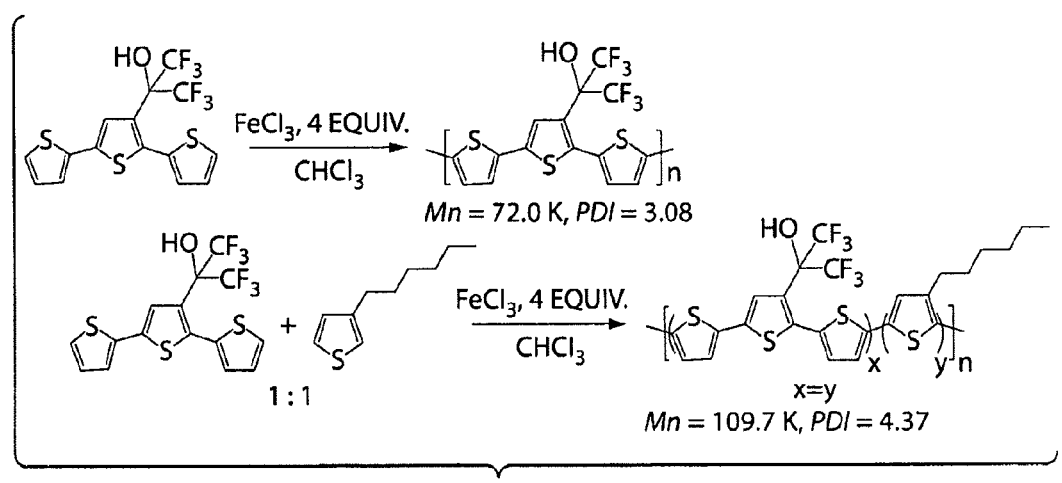
FIG. 28 shows the synthesis of a high molecular weight HFIP polymer, according to one embodiment.
Figure 29A:
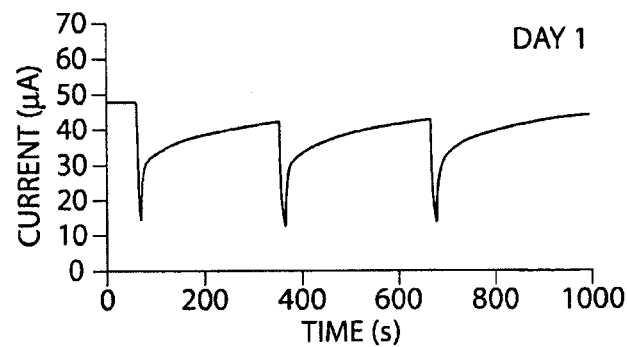
FIG. 29 shows graphs of current vs. time for a sensor comprising HFIP homopolymer upon exposure to DMMP on (A) day 1, (B) day 2, (C) day 3, (D) day 4, (E) day 5, and (F) day 6, according to one embodiment.
Figure 29B:
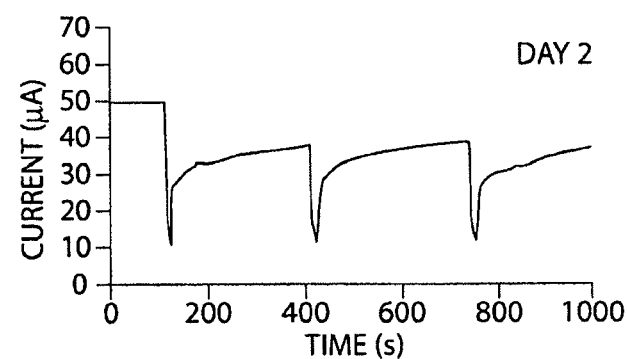
Figure 29C:
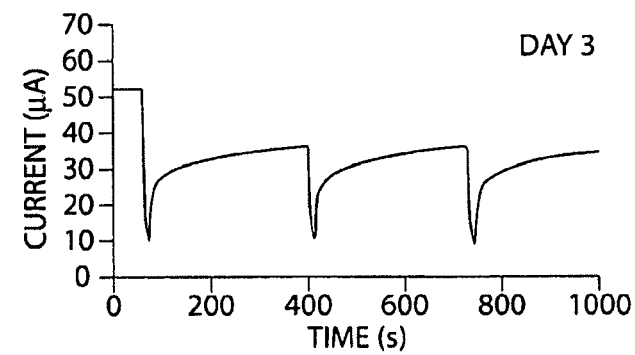
Figure 29D:
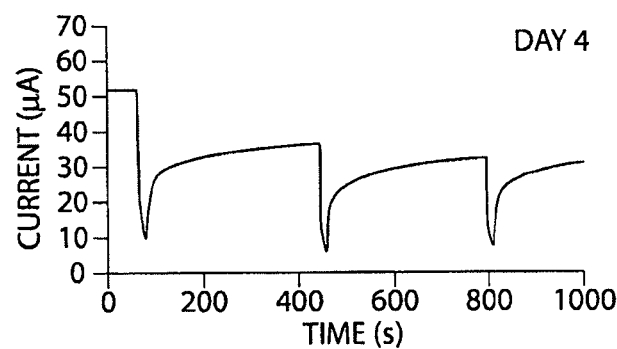
Figure 29E:
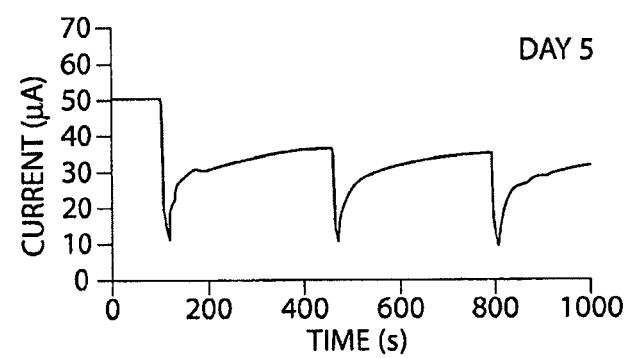
Figure 29F:
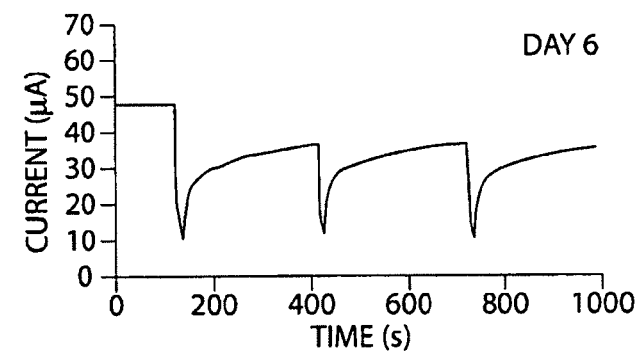
Figure 30A:
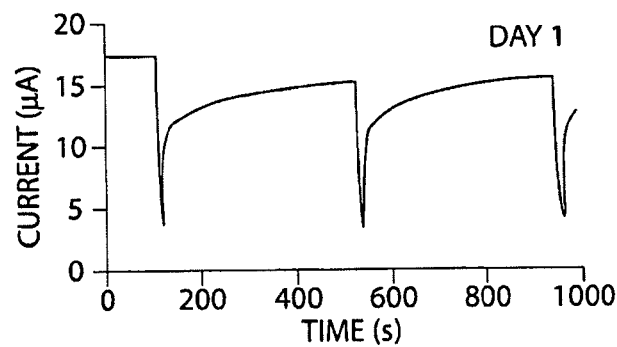
FIG. 30 shows graphs of current vs. time of a sensor comprising HFIP-P3HT copolymer upon exposure to DMMP on (A) day 1, (B) day 2, (C) day 3, (D) day 4, (E) day 5, and (F) day 6, according to one embodiment.
Figure 30B:
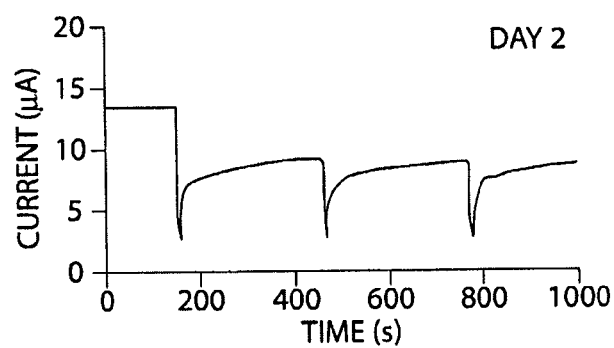
Figure 30C:
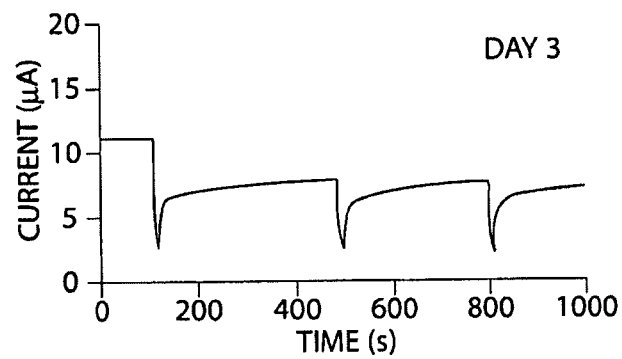
Figure 30D:
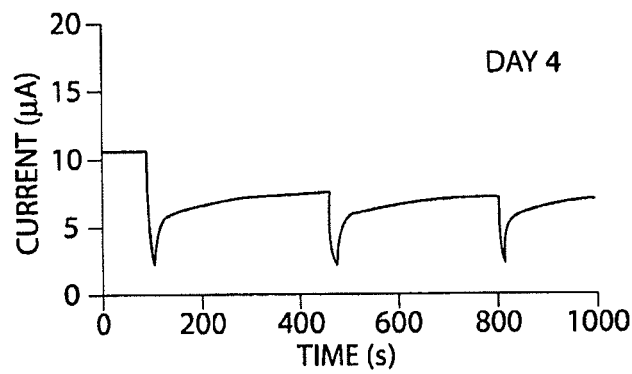
Figure 30E:
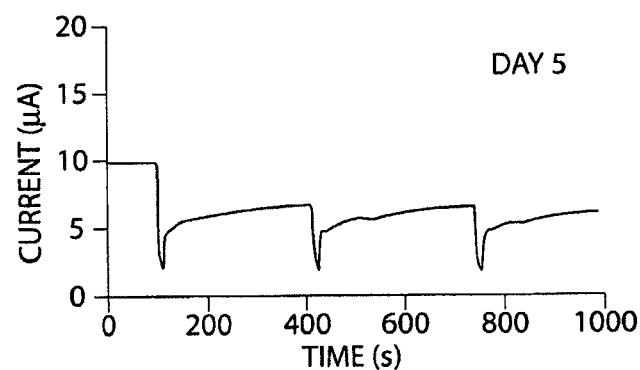
Figure 30F:
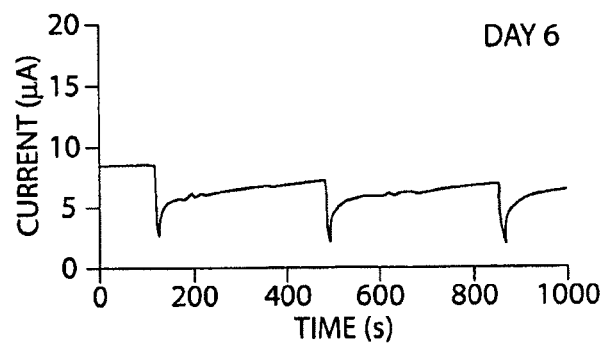
Figure 31A:
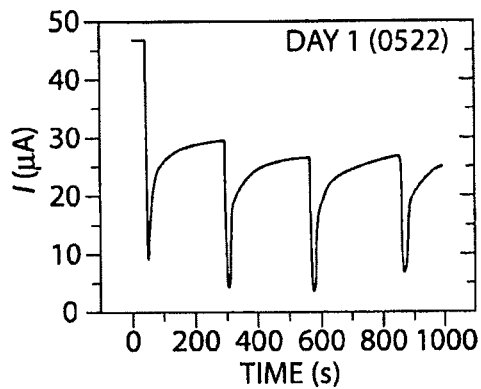
FIG. 31 shows graphs of current vs. time of a sensor comprising HFIP-P3HT copolymer upon exposure to DMMP on (A) day 1, (B) day 2, (C) day 3, (D) day 4, (E) day 5, and (F) day 6, according to another embodiment.
Figure 31B:
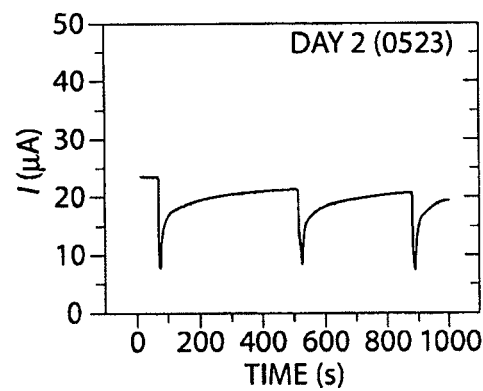
Figure 31C:
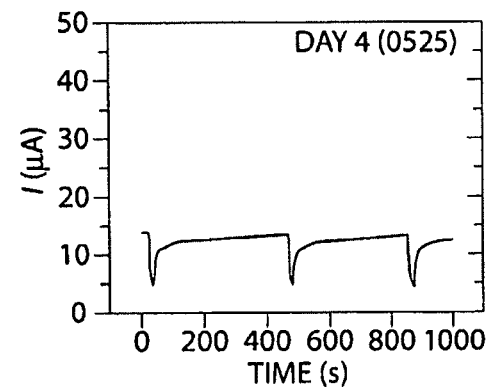
Figure 31D:
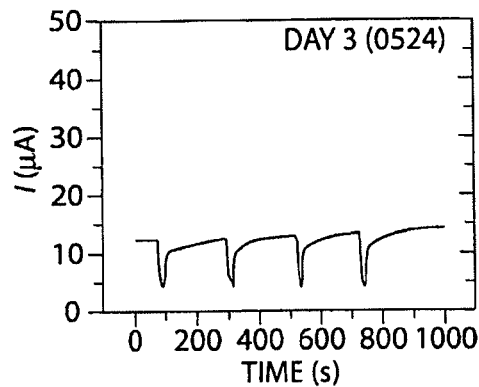
Figure 31E:
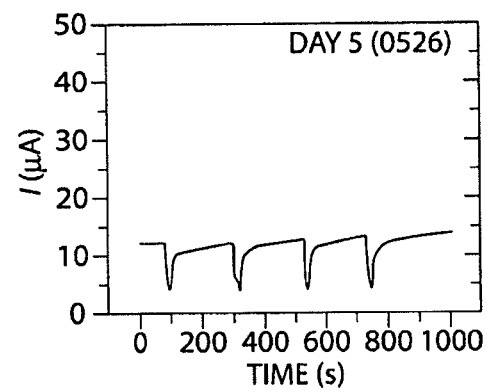
Figure 31F:
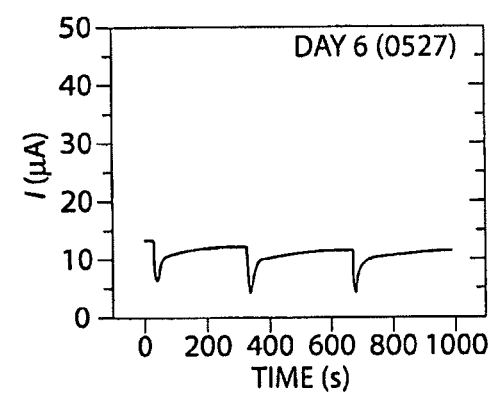

FIG. 28 shows an example of the synthesis of a higher molecular weight polymer. Anhydrous chloroform and 4 equivalents of iron chloride catalyst were utilized to maintain maximum catalytic activity during polymer synthesis. To achieve higher molecular weights, the polymer was fractioned by sequentially precipitating the polymer in solvent mixtures containing increasing amounts of "good" solvent (e.g., hexane, hexane/ethyl acetate (16:1) and hexane/ethyl acetate (6:1)). In this way, an HFIP polymer of number average molecular weight (Mn) as high as 72,000 was prepared. This may be compared to the polymer synthesized in Example 7 which had a molecular weight (Mn) of 25.3K. Using the same method, a random co-polymer of HFIP monomer and 3-hexylthiophene monomer was synthesized to study the stabilizing effect of polymer side chains. In this case, polymers were synthesized with molecular weights in excess of 100,000

Durability Studies of High Molecular Weight Polymer Based Sensor.

In this example, increased stability was observed for sensors comprising higher molecular weight polythiophenes, especially the sensor comprising the HFIP homopolymer.

Sensor Fabrication.

A dispersion was prepared with 1 mg polymer and 1 mg SWCNTs per milliliter of solvent (THF). 20 µL of each dispersions was spin-coated onto gold electrodes. The sensors were then annealed at 100° C. for 3 minutes.

Test Method.

The sensors were exposed to saturated DMMP vapor for 10 seconds and subsequently refreshed in air for ~300-400 seconds. This test was repeated every 24 hours over 6 days. When not being tested, the sensors were kept on bench-top under ambient conditions.

Result of HFIP Homopolymer.

The number average molecular weight of the HFIP homopolymer was 72,000. The dispersion remained stable for at least 2 weeks. FIG. 29 shows graphs of the current vs. time for a sensor comprising HFIP homopolymer when exposed to DMMP on (A) day 1, (B) day 2, (C) day 3, (D) day 4, (E) day 5, and (F) day 6, or testing, according to one embodiment. The performance of the sensor did not significantly decrease over a 6 day period. In some cases, a decrease in the recover rate was observed.

Result of HFIP-P3HT Copolymer.

The number average molecular weight of the HFIP-P3HT copolymer was 109,700. In this example, some precipitation was observed from the dispersion after 4 days. FIGS. 30 and 31 shows graphs of the current vs. time of a sensor comprising HFIP-P3HT copolymer based sensor when exposed to DMMP on (A) day 1, (B) day 2, (C) day 3, (D) day 4, (E) day 5, and (F) day 6, or testing, according to one embodiment.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A device for determining an analyte, comprising:
a first electrode and a second electrode,
a sensor material in electrochemical communication with the first and the second electrodes, wherein resistance to current flow between the first and second electrode is affected by the sensor material;
wherein the sensor material comprises a plurality of non-functionalized carbon nanotubes and a polymer material integrally connected to at least a portion of the plurality of non-functionalized carbon nanotubes, such that the carbon nanotubes are substantially contained within the polymer material, wherein the polymer material comprises a conjugated polymer comprising hexafluoroisopropanol substituents; and
wherein the analyte, if present, interacts with the sensor material to affect resistance to current flow between the first and second electrodes, thereby generating a signal in the device by which the analyte is determined.

2. A device as in claim 1, wherein the conjugated polymer is a polythiophene.

3. A device as in claim 1, wherein the conjugated polymer is a copolymer of thiophene.

4. A device as in claim 1, wherein the polymer material comprises one or more chemical functional groups capable of interacting with the analyte.

5. A device as in claim 1, wherein the sensor material further comprises a binding site.

6. A device as in claim 5, wherein the binding site comprises a calixarene receptor.

7. A device as in claim 5, wherein the binding site comprises a metal-capped calixarene.

8. A device as in claim 5, wherein the binding site comprises a hexafluoroisopropanol group.

9. A device as in claim 5, wherein the binding site comprises a peptide.

10. A device as in claim 5, wherein the binding site comprise a protein.

11. A device as in claim 5, wherein the binding site comprises DNA.

12. A device as in claim 5, wherein the binding site comprises RNA.

13. A device as in claim 5, wherein the binding site comprises PNA.

14. A device as in claim 5, wherein the binding site comprises a transition metal complex.

15. A device as in claim 14, wherein the transition metal complex comprises palladium.

16. A device as in claim 14, wherein the transition metal complex is $PdCl_2$(ethylene)(pyridine).

17. A system for determining at least one analyte, comprising a plurality of devices as in claim 1.

18. A device as in claim 1, wherein the device has a resistance, and the interaction between the analyte and the polymer produces a decrease in resistance.

19. A device as in claim 1, wherein the device has a resistance, and the interaction between the analyte and the polymer produces an increase in resistance.

20. A device as in claim 1, wherein the carbon nanotubes are single-wall carbon nanotubes.

21. A device as in claim 1, wherein the carbon nanotubes are multi-wall carbon nanotubes.

22. A device as in claim 1, wherein the device further comprises an insulating material in contact with at least a portion of the device.

23. A device as in claim 1, wherein the device further comprises a gate electrode in contact with at least a portion of the device.

24. A device for determining an analyte, comprising:
a first electrode and a second electrode,
a sensor material in electrochemical communication with the first and the second electrodes, wherein resistance to current flow between the first and second electrode is affected by the sensor material;
wherein the sensor material comprises a plurality of non-functionalized, single-walled carbon nanotubes and a conjugated polymer material integrally connected to at least a portion of the plurality of non-functionalized, single-walled carbon nanotubes, such that the non-functionalized, single-walled carbon nanotubes are substantially contained within the conjugated polymer material; and
wherein the analyte, if present, interacts with the sensor material to affect resistance to current flow between the first and second electrodes, thereby generating a signal in the device by which the analyte is determined.

25. A device as in claim 24, wherein the conjugated polymer is a polythiophene or a copolymer of thiophene.

26. A device as in claim 24, wherein the conjugated polymer is hexafluoroisopropanol substituted polythiophene.

27. A device as in claim 24, wherein the conjugated polymer is poly(3-hexylthiophene).

28. A device as in claim 24, wherein the sensor material further comprises a binding site.

29. A device as in claim 24, wherein the binding site comprises a calixarene receptor, a hexafluoroisopropanol group, a peptide, protein, DNA, RNA, PNA, or a transition metal complex.

30. A device as in claim 29, wherein the transition metal complex is $PdCl_2$(ethylene)(pyridine).

31. A device as in claim 24, wherein the device has a resistance, and the interaction between the analyte and the polymer produces a decrease in resistance.

32. A device as in claim 24, wherein the device has a resistance, and the interaction between the analyte and the polymer produces an increase in resistance.

33. A device as in claim 24, wherein the device further comprises an insulating material in contact with at least a portion of the device.

34. A device as in claim 24, wherein the device further comprises a gate electrode in contact with at least a portion of the device.

35. A system for determining at least one analyte, comprising a plurality of devices as in claim 24.

* * * * *